(12) United States Patent
Sato

(10) Patent No.: US 6,333,499 B1
(45) Date of Patent: Dec. 25, 2001

(54) METHOD OF DETECTING A SCANNING START POINT, SCANNER, METHOD OF READING OUT IMAGE INFORMATION, AND IMAGE INFORMATION READER

(75) Inventor: Shu Sato, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/461,409

(22) Filed: Dec. 15, 1999

(30) Foreign Application Priority Data

Dec. 15, 1998 (JP) .................................. 10-356774
Dec. 15, 1998 (JP) .................................. 10-356775

(51) Int. Cl.$^7$ .................................................. G01N 21/27
(52) U.S. Cl. ........................ 250/234; 422/82.05; 356/318
(58) Field of Search ....................... 250/231.16, 234–236, 250/483.1; 356/318, 319; 435/286.1, 286.2, 287.1; 422/82.05, 82.06, 82.07, 82.08, 82.09

(56) References Cited

U.S. PATENT DOCUMENTS 5,500,188 * 3/1996 Hafeman et al. ................. 422/82.02
6,083,763 * 7/2000 Balch ................................. 422/105
6,194,233 * 2/2001 Herrmann et al. .................. 356/318
6,248,521 * 6/2001 Van Ness et al. .................. 435/71.1

* cited by examiner

*Primary Examiner*—Stephone B. Allen
(74) *Attorney, Agent, or Firm*—Sughrue Mion, PLLC

(57) ABSTRACT

An image information reader capable of accurately performing reading in going and returning directions so that there is no pixel difference between image information read out in the going direction and image information read out in the returning direction. The image information reader includes an offset measurement section 72 and a second reading-start-point detection section 73. The offset measurement section 72 detects the distance of an optical head 50, moved between a reading end point X1' in the going direction and reversal Xm, as a pulse count C2 from an encoder 55. The second reading-start-point detection section 73 detects a position, where a value C3 counted from reversal in the returning direction by the offset measurement section 72 coincides with C2, as a reading start point in the returning direction.

32 Claims, 8 Drawing Sheets

METHOD OF DETECTING A SCANNING START POINT, SCANNER, METHOD OF READING OUT IMAGE INFORMATION, AND IMAGE INFORMATION READER

BACKGROUND OF THE INVENTION

1. Field of the Invention

The present invention relates to a scanning-start-point detecting method, a scanner, and an image information reading method and an image information reader employing the scanning-start-point detecting method.

2. Description of the Related Art

With the rapid development of techniques in the genetic engineering field in recent years, an enzyme-immunity measuring method, a fluorescent antibody method and the like taking advantage of an antigen-antibody reaction have been utilized in diagnoses and research. Techniques of searching for deoxyribonucleic acid (DNA) having influence on various genetic diseases have also advanced. As one of the methods, attention has been paid to a micro array technique.

The micro array technique is a technique which employs a micro array chip (also called a DNA chip), such as that shown in FIG. 4, previously coated with a great number of interpreted cDNA fragments (an example of specific bound matters) differing from one another at high density (intervals of less than a few 100 $\mu$m) in matrix form at predetermined intervals as dots on a membrane filter, or a slide glass. For instance, DNA fragments (an example of organism-originated matters) are taken out from the cell of healthy subject A and labeled with fluorochrome a, while DNA fragments are taken out from the cell of subject B having a genetic disease and labeled with fluorochrome b. The labeled DNA fragments are dropped on the micro array chip by means of a pipette or the like, whereby the DNA fragments of each subject and the CDNA fragments on the micro array chip are hybridized. Then, each cDNA fragment on the micro array chip is repeatedly scanned by light beams which excite the fluorochromes a and b, respectively. Next, fluorescence emitted from each CDNA fragment is detected by photoelectric read means such as a photomultiplier tube (PMT), a charge-coupled device (CCD) and the like. Based on the results of detection corresponding to the positions of the emitted fluorescence on the micro array chip, it is judged which of the CDNA fragments has been hybridized by the DNA fragment of each subject. By comparing the cDNA fragments hybridized between both subjects, the DNA fragment manifested or lost by the above-mentioned disease is specified.

In the relative, repetitive scanning between the above-mentioned exciting light and micro array chip, incidentally, there is a need to detect a position at which reading starts (a reading start point) in order to obtain the start timing of the collection of read data. The reading start point forms part of the scanning line that exciting light passes through. Therefore, an optical sensor or the like is provided in a portion having a fixed positional relation with the disposed position of the micro array chip. It is common practice for the position, obtained after the scanning time or clock count corresponding to the above-mentioned positional relation has elapsed or counted since the passage of exciting light was detected by the optical sensor, to be detected as a reading start point.

Also, the aforementioned reading-start-point detecting method is not limited to reading the above-mentioned micro array chip but is performed similarly in the case where the relative, horizontal scanning between a reading medium and a head which reads out recorded information from the reading medium is repeatedly performed in a fixed direction so that the information is read out from the reading medium, or in the case where the relative, horizontal scanning between a recording medium and a head which records information on the recording medium is repeatedly performed in a fixed direction so that the information is recorded on the recording medium.

However, the reading-start-point detecting method and the recording-start-point detecting method (both referred to generically as a scanning-start-point detecting method) have to provide a detector, such as an optical sensor for detecting a scanning start point, separately from the horizontal scanning means, as describe above. Furthermore, there is a need to ensure space for installing this detector in the horizontal scanning line, which means that the detector will be a hindrance to achieving device miniaturization. In addition, in scanners, which deal with various kinds of reading media or recording media (both referred to generically as media to be scanned) differing in length in the scanning direction, there is a need to attach detectors at positions corresponding to these media to be scanned, respectively, and consequently, there is a problem that (1) the number of hardware components increases, (2) the cost rises accordingly, and (3) it takes time to design and manufacture the device.

Moreover, the above-mentioned relative, repetitive scanning between exciting light and a micro array chip is performed by a combination of horizontal scanning which is repeatedly moved within a fixed range in the going and returning directions and vertical scanning in a direction perpendicular to the horizontal scanning direction, but reading is performed by emitting exciting light only in the going direction of the horizontal scanning.

The chief reason for this is that, in the read operation in the returning direction, the reading start point varies with the length in the scanning direction of a sample to be scanned and therefore it is difficult from the standpoint of costs and installation space to provide start-point detectors at different positions and that there is a problem that a pixel difference will arise between the image information read out in the going direction and the image information read out in the returning direction.

As described above, the reading-start-point detecting method is not limited to reading the micro array chip but is performed similarly in the case where the relative, horizontal scanning between a reading medium and a head which reads out recorded information from the reading medium is repeatedly performed in a fixed direction so that the information is read out from the reading medium, or in the case where the relative, horizontal scanning between a recording medium and a head which records information on the recording medium is repeatedly performed in a fixed direction so that the information is recorded on the recording medium.

However, in order to read out the above-mentioned medium to be scanned, such as a sample, at a higher speed or record information on the medium at a higher speed, it is effective to perform reading or recording in the returning direction as well as in the going direction.

SUMMARY OF THE INVENTION

The present invention has been made in view of the aforementioned circumstances. Accordingly, it is an object of the present invention to provide a scanning-start-point detecting method and a scanner which are capable of detecting a scanning start point without adding a special photo detector. Another object of the invention is to provide an image information reading method and an image information reader employing the scanning-start-point detecting method.

The scanning-start-point detecting method and the scanner of the present invention detect the rotational direction of rotary drive means such as a motor (horizontal scanning means) and then detect a scanning start point, based on a rotational angle pulse signal obtained after the rotational direction has been reversed.

The scanning-start-point detecting method of the present invention is a method of detecting a reading start point which starts reading information in a horizontal scanning direction or a recording start point which starts recording information in the horizontal scanning direction, by relatively moving a predetermined medium to be scanned and/or a scan head, which reads the information from the medium or records the information on the medium, by horizontal scanning means so that the scan head can reiteratively perform horizontal scanning in a fixed direction with respect to the medium. The method comprises the steps of: generating two rotational angle pulse signals having a phase difference which varies according to a rotational direction of a rotary drive means provided in the horizontal scanning means; causing the horizontal scanning direction to depend on the rotational direction of the rotary drive means; detecting reversal of the rotational direction of the rotary drive means based on the phase difference between the two rotational angle pulse signals; detecting the rotational angle pulse signals from the reversal of the rotational direction; and detecting the scanning start point, based on the detected rotational angle pulse signals.

The angle signal generation means comprises, for example, an encoder provided in the drive shaft or the like of rotary drive means, such as a motor or the like, and a photo detector which photoelectrically reads out the passage of slits in the encoder. Such an encoder and a photo detector have hitherto been provided as horizontal scanning means. The two rotational angle pulse signals, which are generated as signals having a phase difference varying according to a rotational direction, are intended to mean two rotational angle pulse signals that are generated for each row when two rows of circumferential slits are provided at different radial positions of an encoder and have a phase difference other than ½ cycle (i.e., a phase difference other than $n\pi$ (rad)).

Note that the scanning-start-point detecting method of the present invention is applicable to a method of reading out image information from a medium, a method of recording information on a medium, and the like, but is not thus limited, as long as a scan head repeatedly scans the medium in a fixed direction. The same also applies to the scanner of the present invention described in the following.

It is preferable to change a timing at which the rotational direction of the rotary drive means switches in accordance with a length in the horizontal scanning direction of the medium. The timing of switching the rotational direction can be performed based on a rotational pulse signal.

The image information reading method of the present invention is a method of reading out image information from a predetermined sample, the method being equipped with an exciting light source for emitting exciting light, an optical head for emitting the exciting light to the sample, horizontal scanning means for relatively moving the optical head and/or the sample so that the exciting light can repeatedly perform horizontal scanning by a predetermined length in a fixed direction with respect to the sample, vertical scanning means for relatively moving the optical head and/or the sample in a direction substantially perpendicular to the horizontal scanning direction so that the exciting light can perform vertical scanning with respect to the sample, and photoelectric read means for photoelectrically reading out luminescence emitted from the sample irradiated with the exciting light by the relative scanning. The method comprises the steps of: generating two rotational angle pulse signals having a phase difference which varies according to a rotational direction of a rotary drive means provided in the horizontal scanning means; causing the horizontal scanning direction to depend on the rotational direction of the rotary drive means; detecting reversal of the rotational direction of the rotary drive means based on the phase difference between the two rotational angle pulse signals; detecting the rotational angle pulse signals from the reversal of the rotational direction; and detecting a reading start point which starts reading the sample, based on the detected rotational angle pulse signals.

In the image information reading method of the present invention, it is preferable to change a timing at which the rotational direction of the rotary drive means switches in accordance with a length in the horizontal scanning direction of the medium. The timing of switching the rotational direction can be performed based on a rotational pulse signal.

The scanner of the present invention is a scanner for detecting a reading start point which starts reading information in a horizontal scanning direction or a recording start point which starts recording information in the horizontal scanning direction, by relatively moving a predetermined medium to be scanned and/or a scan head, which reads the information from the medium or records the information on the medium, by horizontal scanning means so that the scan head can reiteratively perform horizontal scanning in a fixed direction with respect to the medium. The scanner comprises rotary drive means, rotational direction detection means, and scanning-start-point detection means. The rotary drive means has angle signal generation means for generating two rotational angle pulse signals having a phase difference which varies according to a rotational direction of the rotary drive means, the rotary drive means being provided in the horizontal scanning means and the horizontal scanning direction being dependent on the rotational direction of the rotary drive means. The rotational direction detection means detects the rotational direction of the rotary drive means and reversal of the rotational direction, based on the phase difference between the two rotational angle pulse signals. The scanning-start-point detection means detects the rotational angle pulse signals from the reversal detected by the rotational direction detection means, and detects the scanning start point, based on the detected rotational angle pulse signals.

It is preferable that the rotary drive means change the timing at which the rotational direction switches in accordance with a length in the horizontal scanning direction of the medium.

The image information reader according to the present invention comprises an exciting light source, an optical head, horizontal scanning means, vertical scanning means, photoelectric read means, rotary drive means, rotational direction detection means, and reading-start-point detection means. The exciting light source emits exciting light and the optical head emits the exciting light to a predetermined sample. The horizontal scanning means relatively moves the optical head and/or the sample so that the exciting light can repeatedly perform horizontal scanning by a predetermined length in a fixed direction with respect to the sample. The vertical scanning means relatively moves the optical head and/or the sample in a direction substantially perpendicular to a direction of the horizontal scanning so that the exciting light can perform vertical scanning with respect to the sample. The photoelectric read means photoelectrically reads out luminescence emitted from the sample irradiated with the exciting light by the relative scanning. The rotary drive means has angle signal generation means for generating two rotational angle pulse signals having a phase difference which varies according to a rotational direction of the rotary drive means, the rotary drive means being provided in the horizontal scanning means and the horizontal scanning direction being dependent on the rotational direction of the rotary drive means. The rotational direction detection means detects the rotational direction of the rotary drive means and reversal of the rotational direction, based on the phase difference between the two rotational angle pulse signals. The reading-start-point detection means detects the rotational angle pulse signals from the reversal detected by the rotational direction detection means, and detects a reading start point which starts reading the sample, based on the detected rotational angle pulse signals.

In the image information reader, it is preferable that the rotary drive means change the timing at which the rotational direction switches in accordance with a length in the horizontal scanning direction of the sample.

According to the scanning-start-point detecting method, the scanner, the image information reader, and the image information reading method of the present invention, horizontal scanning means has rotary drive means which generates two rotational angle pulse signals differing in phase in accordance with a rotational direction. By detecting the two rotational angle pulse signals and taking advantage of the phase difference between both pulse signals, the rotational direction of the rotary drive means, such as a motor or the like, can be detected. Therefore, the timing at which the rotational direction of the rotary drive means reverses in order to reiteratively perform horizontal scanning in a fixed direction can also be detected. By counting the rotational angle pulse signal from the reversal, for example, the scanning start point (e.g., a reading start point and a recording start point) of a sample, which is at a fixed position from the reversal point, can be detected.

The rotary drive means for generating two rotational angle pulse signals differing in phase in accordance with a rotational direction is previously provided in the horizontal scanning means in order to control the length of horizontal scanning and therefore utilizes the existing component effectively. Thus, there is no need to add additional light-detecting means.

In addition, the present invention has been made in view of the aforementioned circumstances. Accordingly, it is an object of the present invention to provide a scanning-start-point detecting method and a scanner which are capable of accurately reading or recording information in the going and returning directions independently of a length difference in the horizontal scanning direction of a medium to be scanned, without producing a pixel difference between the information read out or recorded in the going direction and the information read out or recorded in the returning direction. Another object of the invention is to provide an image information reading method and an image information reader employing the scanning-start-point detecting method.

The scanning-start-point detecting method and the scanner of the present invention measure the distance of the medium and/or the scan head moved from the scanning end point in the going direction of horizontal scanning to the reversal of the horizontal scanning. A point, moved from the reversal of the horizontal scanning means in the returning direction by the amount of the measured moved distance, is detected as a scanning start point in the returning direction. In this way, the scanning end point in the going direction coincides with the scanning start point in the returning direction. In this manner, information is read out or recorded without any pixel difference between the going and returning directions.

The scanning-start-point detecting method is a method of detecting a reading start point which starts reading information in a horizontal scanning direction or a recording start point which starts recording information in the horizontal scanning direction, by relatively moving a predetermined medium to be scanned and/or a scan head, which reads the information from the medium or records the information on the medium, in the going and returning directions by horizontal scanning means so that the scan head can reiteratively perform horizontal scanning in a fixed direction with respect to the medium. The method comprises the steps of: detecting a scanning start point which starts scanning the medium in the going direction of the horizontal scanning; measuring a moved distance in the going direction of the medium and/or the scan head between a scanning end point, which ends the scanning, and reversal of a moving direction of the medium and/or the scan head from the going direction to the returning direction, the scanning end point previously being set according to a length in the horizontal scanning direction of the medium; measuring a moved distance in the returning direction of the medium and/or the scan head from the reversal of the moving direction of the medium and/or the scan head; and detecting a position, where the moved distance in the returning direction coincides with the moved distance measured in the going direction, as a scanning start point in the returning direction.

The phrase "measuring the moved distance" means that a physical amount corresponding to the moved distance may be measured instead of directly measuring a physical amount of "distance". When horizontal scanning takes advantage of the rotation of rotary drive means, for example, the rotational angle of the rotary drive means may be measured. When the rotational angle corresponds to the pulse count generated by the passage of slits in an encoder, the pulse count may be counted.

The scanning end point may be set based on a distance moved from the detected scanning start point in the going direction.

The moved distance in the returning direction of the medium and/or the scan head, measured from the reversal of the moving direction of the medium and/or the scan head, may be corrected by a previously obtained free running distance at the time of the reversal, and a position, where the corrected moved distance in the returning direction coincides with the moved distance measured in the going direction, may be detected as the scanning start point in the returning direction.

The scanning-start-point detecting method of the present invention is applicable to a method of reading out image information from a medium, a method of recording information on a medium, and the like, but is not to be thus limited as long as a scan head repeatedly scans the medium in a fixed direction. The same also applies to the scanner of the present invention described below.

The scanner of the present invention is a scanner for detecting a reading start point which starts reading information in a horizontal scanning direction or a recording start point which starts recording information in the horizontal scanning direction, by relatively moving a predetermined medium to be scanned and/or a scan head, which reads the information from the medium or records the information on the medium, in the going and returning directions by horizontal scanning means so that the scan head can reiteratively perform horizontal scanning in a fixed direction with respect to the medium. The scanner comprises reversal detection means, first scanning-start-point detection means, first offset measurement means, second offset measurement means, and second scanning-start-point detection means. The reversal detection means detects that a moving direction of the medium and/or the scan head being moved by the horizontal scanning means has been reversed from the going direction to the returning direction. The first scanning-start-point detection means detects a scanning start point in the going direction of the horizontal scanning which is performed by the horizontal scanning means. The first offset measurement means measures a moved distance in the going direction of the medium and/or the scan head between a scanning end point which ends scanning, set according to a length in the horizontal scanning direction of the medium, and the reversal. The second offset measurement means measures a moved distance in the returning direction of the medium and/or the scan head from the reversal detected by the reversal detection means. The second scanning-start-point detection means detects a horizontal scanning position, where the moved distance in the returning direction detected by the second offset measurement means coincides with the moved distance in the going direction detected by the first offset measurement means, as a scanning start point in the returning direction.

The scanning end point may be set based on a distance moved from the scanning start point detected by the first scanning-start-point detection means.

It is preferable that the second scanning-start-point detection means detect the scanning start point in the returning direction by correcting the moved distance in the returning direction, detected by the second offset measurement means, by a previously obtained free running distance at the time of the reversal corresponding to backlash of the horizontal scanning means.

The horizontal scanning means may be equipped with rotary drive means having rotational directions on which the moving directions of the medium and/or the scan head in the going and returning directions depend, and also having a rotational angle on which the moved distance depends. The first and second offset measurement means may measure the moved distance by detecting the rotational angle.

When horizontal scanning means is provided with rotary drive means which has angle signal generation means (e.g., an encoder or the like) for generating two rotational angle pulse signals differing in phase in accordance with a rotational direction, the process of detecting reversal of a rotational direction, i.e., reversal of a moving direction on the basis of the phase difference between the two rotational angle pulse signals, can be applied as the reversal detection means.

Note that the first offset measurement means and the second offset measurement means may be constructed functionally integral with each other.

The image information reading method of the present invention is a method of photoelectrically reading out luminescence emitted from a predetermined sample irradiated with exciting light, by relatively moving the exciting light and/or the sample within a fixed range in the going and returning directions so that the exciting light can reiteratively perform horizontal scanning relatively with respect to the sample and by relatively moving the exciting light and/or the sample in a direction substantially perpendicular to a direction of the horizontal scanning so that the exciting light can perform vertical scanning with respect to the sample. The method comprises the steps of: detecting a reading start point which starts reading the luminescence in the going direction of the horizontal scanning; reading out the luminescence photoelectrically, while the exciting light is scanning the sample from the detected reading start point to a reading end point which ends the reading, the reading end point previously being set according to a length in the horizontal scanning direction of the sample; measuring a moved distance in the going direction of the exciting light and/or the sample between the reading end point and reversal of a moving direction of the exciting light and/or the sample from the going direction to the returning direction; measuring a moved distance in the returning direction of the exciting light and/or the sample from the reversal of the moving direction of the exciting light and/or the sample; and starting reading the luminescence photoelectrically in the returning direction from a position where the moved distance in the returning direction coincides with the moved distance measured in the going direction.

In the image information reading method, the phrase "by relatively moving the exciting light and/or the sample within a fixed range in the going and returning directions and by relatively moving the exciting light and/or the sample in a direction substantially perpendicular to a direction of horizontal scanning" does not always mean that horizontal scanning and vertical scanning are simultaneously performed in parallel but can mean that vertical scanning is performed at any time during single horizontal scanning in the going and returning directions.

In the image information reading method, the phrase "measuring the moved distance" means that a physical amount corresponding to the moved distance may be measured instead of directly measuring a physical amount of "distance." When horizontal scanning takes advantage of the rotation of rotary drive means, for example, the rotational angle of the rotary drive means may be measured. When the rotational angle corresponds to the pulse count generated by the passage of slits in an encoder, the pulse count may be counted.

In the image information reading method, the reading end point may be set based on a distance moved from the detected reading start point in the going direction.

When the horizontal scanning means for performing horizontal scanning has backlash and therefore has a free running distance at the time of the reversal of the moving direction of the horizontal scanning means, the moved distance in the returning direction of the exciting light and/or the sample, measured from the reversal of the moving direction of the exciting light and/or the sample, may be corrected by the free running distance. It is preferable to start reading the luminescence photoelectrically in the returning direction from a position where the corrected moved distance in the returning direction coincides with the moved distance measured in the going direction.

The image information reader of the present invention comprises an exciting light source, an optical head, horizontal scanning means, vertical scanning means, photoelectric read means, reversal detection means, first reading-start-point detection means, first offset measurement means, second offset measurement means, and second reading-start-point detection means. The exciting light source emits exciting light. The optical head emits the exciting light to a predetermined sample. The horizontal scanning means relatively moves the exciting light and/or the sample within a fixed range in the going and returning directions so that the exciting light can reiteratively perform horizontal scanning with respect to the sample. The vertical scanning means relatively moves the exciting light and/or the sample in a direction substantially perpendicular to a direction of the horizontal scanning so that the exciting light can perform vertical scanning with respect to the sample. The photoelectric read means photoelectrically reads out luminescence emitted from the sample irradiated with the exciting light by the relative scanning. The reversal detection means detects that a moving direction of the exciting light and/or the sample being moved by the horizontal scanning means has been reversed from the going direction to the returning direction. The first reading-start-point detection means detects a reading start point which starts reading the luminescence in the going direction of the horizontal scanning which is performed by the horizontal scanning means. The first offset measurement means measures a moved distance in the going direction of the exciting light and/or the sample between a reading end point which ends reading, set according to a length in the horizontal scanning direction of the sample, and the reversal. The second offset measurement means measures a moved distance in the returning direction of the exciting light and/or the sample from the reversal detected by the reversal detection means. The second reading-start-point detection means detects a horizontal scanning position, where the moved distance in the returning direction detected by the second offset measurement means coincides with the moved distance in the going direction detected by the first offset measurement means, as a reading start point which starts the reading in the returning direction. The photoelectric read means starts the reading from the reading start points in the going and returning directions.

In the image information reader, the reading end point may be set based on a distance moved from the reading start point detected by the first reading-start-point detection means.

In the image information reader, it is preferable that the second reading-start-point detection means detect the reading start point in the returning direction by correcting the moved distance in the returning direction, detected by the second offset measurement means, by a previously obtained free running distance at the time of the reversal corresponding to backlash of the horizontal scanning means.

Furthermore, the horizontal scanning means may be equipped with rotary drive means having rotational directions on which the moving directions of the exciting light and/or the sample in the going and returning directions depend and also having a rotational angle on which the moved distance depends, and the first and second offset measurement means may measure the moved distance by detecting the rotational angle.

When, in the image information reader, the horizontal scanning means is provided with rotary drive means which has angle signal generation means (e.g., an encoder or the like) for generating two rotational angle pulse signals differing in phase in accordance with a rotational direction, the process of detecting reversal of a rotational direction, i.e., reversal of a moving direction on the basis of the phase difference between the two rotational angle pulse signals can be applied as the reversal detection means.

In the image information reader, the first offset measurement means and the second offset measurement means may be constructed functionally integral with each other.

According to the scanning-start-point detecting method, the scanner, the image information reader, and the image information reading method of the present invention, the distance of the medium and/or the scan head, moved between the scanning end point in the going direction of horizontal scanning and the reversal of the horizontal scanning, is measured. A point, moved from the reversal of the horizontal scanning means in the returning direction by the amount of the measured moved distance, is detected as a scanning start point in the returning direction. In this way, the scanning end point in the going direction coincides with the scanning start point in the returning direction. In the going and returning directions, therefore, information can be read out or recorded without any pixel difference.

In addition, even when there is a length difference in the horizontal scanning direction between mediums to be scanned, there is no need to provide a component, such as a reference section which becomes a different scanning start point reference in the returning direction, for each length.

Furthermore, a new scanning start point in the going direction is detected each time the medium or the scan head is moved in the going and returning directions. Therefore, as horizontal scanning goes further, no pixel difference is produced between the going and returning directions. Furthermore, there is no possibility that a pixel difference will cumulate.

The above and many other objects, features and advantages of the present invention will become manifest to those skilled in the art upon making reference to the following detailed description and accompanying drawings in which preferred embodiments incorporating the principle of the present invention are shown by way of illustrative example.

DETAILED DESCRIPTION OF THE PREFERRED EMBODIMENTS

A first embodiment of a scanner of the present invention that carries out a scanning-start-point detecting method will hereinafter be described with reference to the drawings.

Figure 1A:
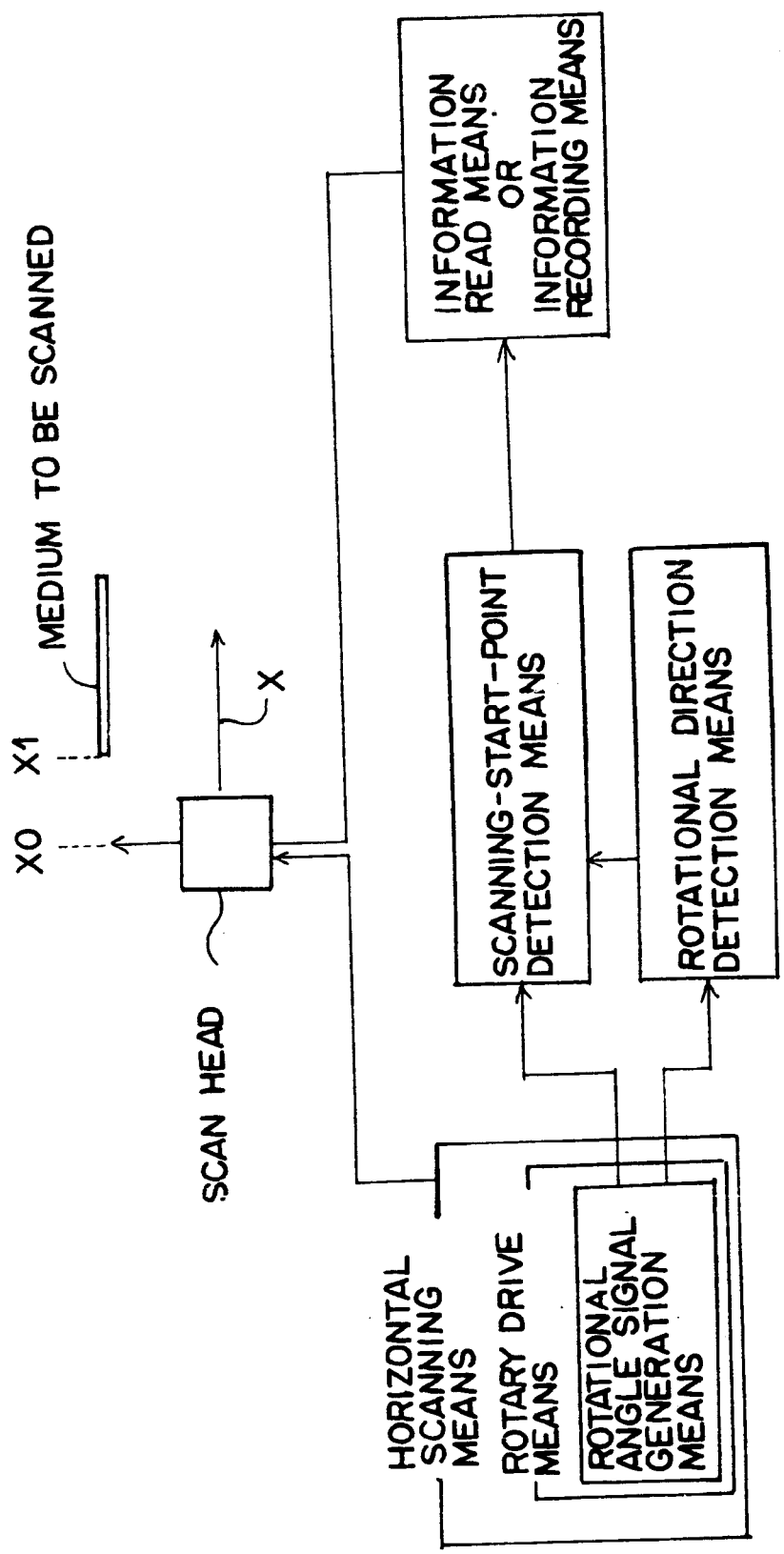
FIG. 1A is a block diagram showing a first embodiment of a scanner of the present invention.

FIG. 1A shows the first embodiment of the scanner of the present invention. The scanner shown in the figure detects a reading start point which starts reading information or a recording start point which starts recording information (hereinafter referred to generically as a scanning start position X1) in the direction of horizontal scanning (i.e., the direction of arrow X), by relatively moving a scan head, which reads out information from a medium to be scanned or records information on the medium by horizontal scanning means so that the scan head can reiteratively perform horizontal scanning in the direction of arrow X with respect to the medium. The horizontal scanning means includes rotary drive means having rotational-angle-signal generation means which generates two rotational angle pulse signals differing in phase in accordance with the rotational direction of the rotary drive means. The directions of the horizontal scanning (X direction and the opposite direction) are dependent on the rotational direction of the rotary drive means. The scanner further includes rotational direction detection means and scanning-start-point detection means. The rotational direction detection means detects the rotational direction of the rotary drive means and the reversal of this rotational direction, based on the phase difference between two rotational angle pulse signals. The scanning-start-point detection means detects a rotational angle pulse signal output when the reversal (corresponding to the reversal position X0 in the horizontal scanning direction) is detected by the rotational angle detection means, and detects the scanning start point X1, based on the detected rotational angle pulse signal.

Now, the operation of the first embodiment will be described.

The horizontal scanning means moves the scan head, which is at a standstill at a reference point (hereinafter referred to as simply a start point), in the direction of arrow X by rotation of the rotary drive means. When the rotary drive means starts rotating, the rotational-angle-signal generation means generates two rotational angle pulse signals differing in phase from each other in accordance with the rotational direction of the rotary drive means. The two rotational angle pulse signals are input to the rotational direction detection means and the scanning-start-point detection means.

The rotational direction detection means detects, by the input of the rotational angle pulse signals, that the rotational drive means has started rotating and also detects the rotational direction of the rotational drive means, based on the phase difference between the input 2 rotational angle pulse signals. Because the scan head has initially been positioned at the start point X0, it is detected that the scan head has been moved toward the direction of arrow X. The result of detection is input to the scanning-start-point detection means.

The scanning-start-point detection means starts counting the rotational angle pulse signal being input from the rotational-angle-signal generation means in response to the input of the detection result from the rotational direction detection means. Also when the pulse count reaches a pulse count corresponding to a distance from the start point X0 in the horizontal direction to the scanning start point X1 of actually starting horizontal scanning with respect to a medium to be scanned, the scanning-start-point detection means inputs an instruction signal, which starts reading information recorded on the medium through the scan head, to an information reader, or inputs an instruction signal, which starts recording information on the medium through the scan head, to an information recorder.

Upon receiving the instruction signal, the information reader starts reading information recorded on the medium through the scan head, or the information recorder starts recording information on the medium through the scan head.

When the horizontal scanning in the X direction ends, the rotational direction of the rotary drive means is reversed, whereby the scan head is moved in the direction opposite from the direction of arrow X. Simultaneously, the rotational-angle-signal generation means generates 2 rotational angle pulse signals having a phase difference which differs from the aforementioned phase difference. Based on the phase difference between the 2 rotational angle pulse signals, the rotational direction detection means detects the reversal of the rotational direction of the rotary drive means.

When the scan head returns to the start point X0, the rotary drive means rotates in reverse again and the phase difference between 2 rotational angle pulse signals generated by the rotational-angle-signal generation means also changes. The change in the phase difference is detected by the rotational direction detection means and the reversal of the rotational direction of the rotary drive means is detected. The result of detection is input to the scanning-start-point detection means. Based on the input result of detection, the scanning-start-point detection means starts counting the pulse signal input from the rotational-angle-signal generation means and detects a scanning start point similarly to the above-mentioned operation.

According to the scanner of the first embodiment, as described above, the horizontal scanning means has the rotary drive means that generates 2 rotational angle pulse signals differing in phase from each other in accordance with the rotational direction of the rotary drive means. Therefore, the rotational direction of rotary drive means, such as a motor, can be detected by detecting the 2 rotational angle pulse signals and then detecting the phase difference between both pulse signals. In addition, since horizontal scanning is reiteratively performed in a fixed direction, the timing at which the rotational direction of the rotary drive means is reversed can be detected. By counting the rotational angle pulse signal from the reversal, the scanning start point of a sample (i.e., a reading start point or a recording start point) having a fixed distance from the position of reversal can be detected.

Now, a specific embodiment of an image information reader incorporating the above-mentioned scanner will be described with reference to the drawings.

Figure 2A:
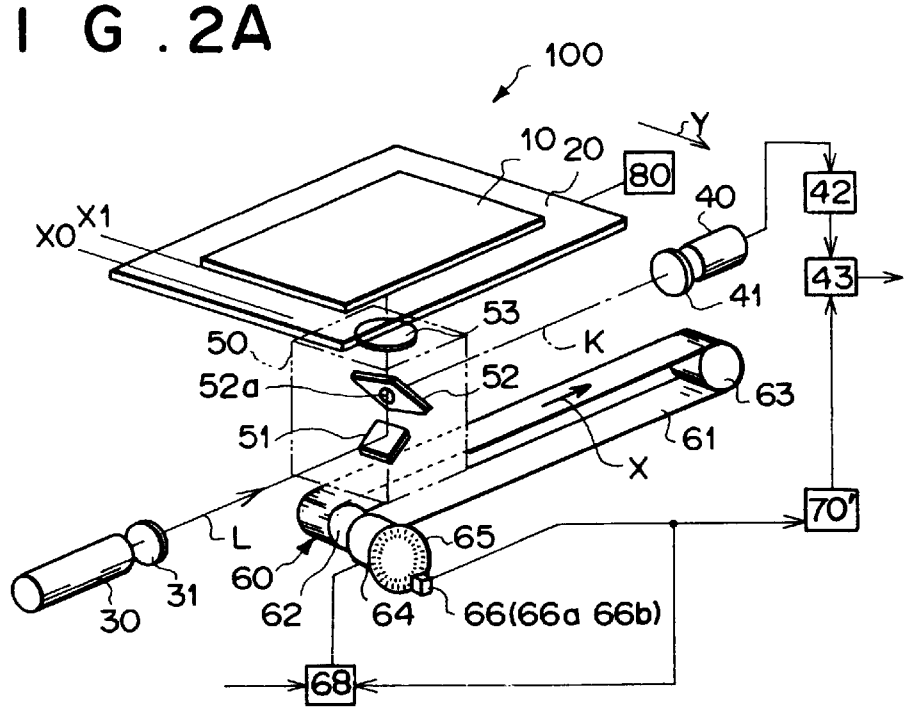
FIG. 2A is a perspective view of a first embodiment of an image information reader of the present invention.
Figure 2B:
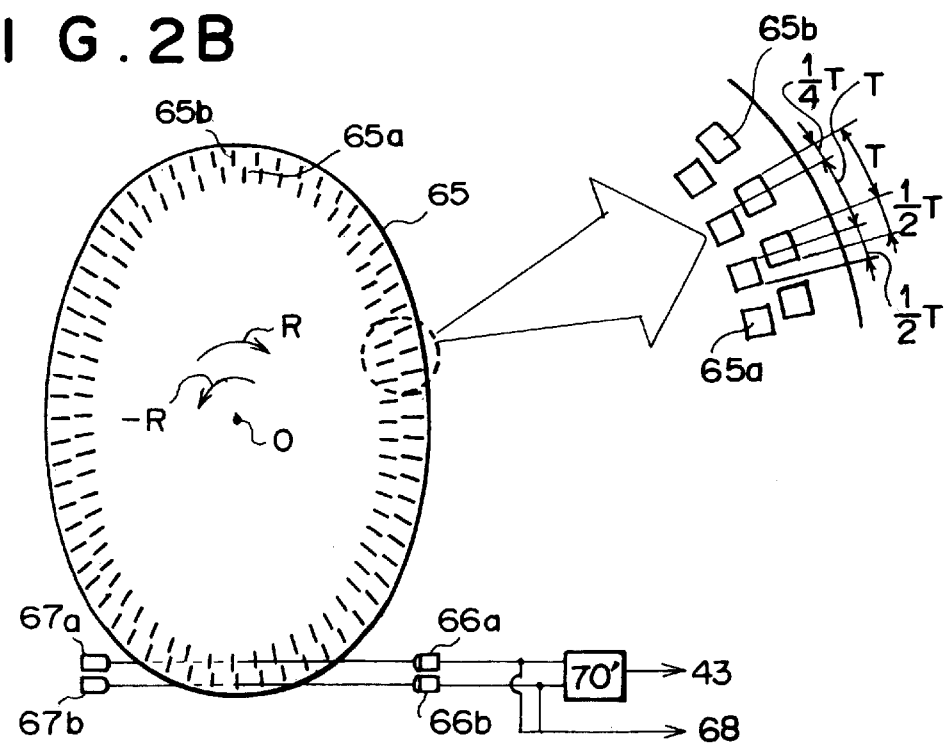
FIG. 2B shows an enlarged view of the encoder and vicinity of the image information reader shown in FIG. 2A.
Figure 3A:
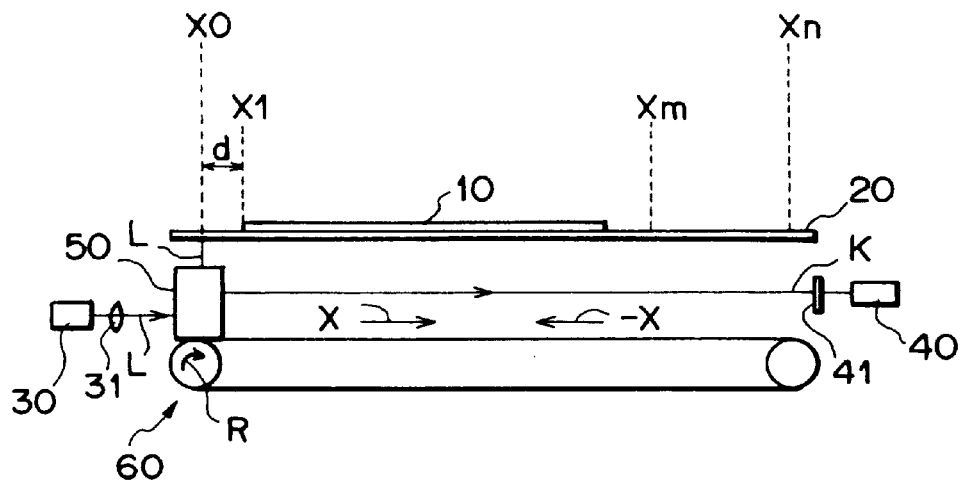
FIG. 3A is a diagram for describing the operation of the image information reader shown in FIG. 2A.

FIG. 2A shows a first embodiment of the image information reader of the present invention, FIG. 2B shows the encoder and vicinity of the image information reader shown in FIG. 2A, and FIG. 3A is used for describing the operation of the image information reader shown in FIG. 2A.

Figure 4:
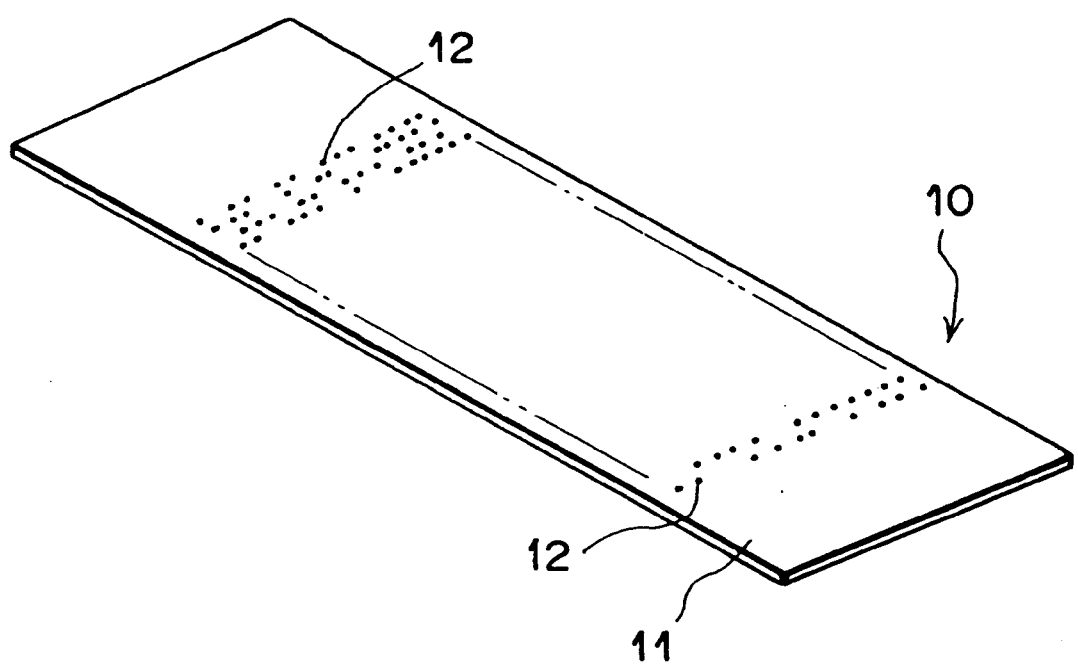
FIG. 4 is a perspective view showing a micro array chip that is read out by the image information reader shown in FIG. 2C.

The image information reader 100 shown in FIG. 2A comprises: (1) a transparent sample tray 20 on which a micro array chip 10, such as that shown in FIG. 4, is placed so that the edge of the chip 10 coincides with a predetermined reference position X1, the chip 10 including a predetermined hybridized DNA (an example of organism-originated matters) labeled with a fluorochrome; (2) a laser light source 30 which emits laser light L having a wavelength band that excites the above-mentioned fluorochrome; (3) a lens 31 which forms the laser light L emitted from the light source 30 into a beam of light; (4) a photomultiplier tube (hereinafter referred to as a PMT) 40 which photoelectrically detects fluorescence K emitted from the fluorochrome of the micro array chip 10 excited with the laser light beam L; (5) an optical head 50 which emits the laser light beam L to the micro array chip 10 placed on the sample tray 20 and guides fluorescence K, emitted from the micro array chip 10 irradiated with the laser light beam L, to the PMT 40; (6) a laser-light cut filter 41 disposed in the optical path between the optical head 50 and the PMT 40; (7) horizontal scanning means 60 which reiteratively moves the optical head 50 at uniform velocity in the direction of arrow X; (8) vertical scanning means 80 which moves the micro array chip 10 and the sample tray 20 in the direction of arrow Y substantially perpendicular to the direction of arrow X; (9) a rotational direction detection function which detects the rotational direction of a motor 64 constituting part of the horizontal scanning means 60; (10) reading-start-point detection means 70' which detects a reading start point that starts reading fluorescence K emitted from the micro array chip 10, based on the reversal time of the detected rotational direction and the rotational angle of the motor 64; (11) rotational direction switching means 68 which performs control of reversing the rotational direction of the motor 64, based on the rotational angle of the motor 64; (12) an amplifier 42 which logarithmically amplifies a detection signal detected by the PMT 40; and (13) an A/D converter 43 which converts the amplified detection signal to a digital signal at predetermined timing.

Here, the light source 30 is disposed such that the laser light L therefrom is emitted in a direction along the direction of arrow X, and the PMT 40 is disposed such that it detects fluorescence K incident along the direction of arrow X.

The optical head 50 includes a plane mirror 51, a perforated mirror 52, and a collimator lens 53. The plane mirror 51 reflects the laser light beam L, traveling in the direction of arrow X, in a direction perpendicular to the micro array chip 10 (which is an upward direction in FIG. 2A). The perforated mirror 52 is formed with an aperture 52a that the laser light beam L reflected by the plane mirror 51 passes through. This perforated mirror 52 reflects the greater part of the fluorescence K, emitted downward from the lower surface of the micro array chip 10, in the direction of arrow X so that the reflected fluorescence K is incident on the PMT 40. The collimator lens 53 forms the fluorescence K emitted from the lower surface of the micro array chip 10 into an almost collimated beam of light. The plane mirror 51, the perforated mirror 52, and the lens 53 are constructed integrally with one another.

The laser-light cut filter 41 is a filter with a band limited so as to permit the passage of fluorescence K but prevent the passage of laser light L, in order to prevent the laser light L being incident on the PMT 40 even when part of the laser light L, scattered and reflected at the micro array chip 10 and the sample tray 20, travels toward the PMT 40 along with fluorescence K.

The horizontal scanning means 60 includes (1) a motor 64; (2) a drive pulley 62 that is driven to rotate by this motor 64; (3) a conveyor belt 61, looped between the drive pulley 62 and an idle pulley 63, for integrally moving the optical head 50 in the direction of arrow X in accordance with the rotation in the direction of arrow R (clockwise direction) of the drive pulley 62 and also in the direction of arrow –X in accordance with the rotation in the direction of arrow –R (counterclockwise direction) of the drive pulley 62; (4) an encoder 65 (see FIG. 2B) mounted at its center on the drive shaft of the motor 64; and (5) light-emitting diodes 67a, 67b and photodiode 66a, 66b which generate rotational angle pulse signals by rotation of the encoder 65 and detect the generated rotational angle pulse signals.

The encoder 65, as shown in FIG. 2B, is provided with two rows of inner and outer slits 65a, 65b, which are disposed at different radial positions from the center 0 of the encoder 65 in the circumferential direction of the encoder 65. The inner circumferential slit row 65a and the outer circumferential slit row 65b are both formed at equal spaces over the entire circumference of the encoder 65. There is a phase difference of ¼ cycle between the inner circumferential slit row 65a and the outer circumferential slit row 65b.

The upper light-emitting diode 67a and the upper photodiode 66a correspond to the inner circumferential slit row 65a of the encoder 65, while the lower light-emitting diode 67b and the lower photodiode 66b correspond to the outer circumferential slit row 65b. With this arrangement, a single pulse (high level) is detected every time the slit of each slit row passes through the optical path between the light-emitting diode and the photodiode. Note that the scanner of the first embodiment generates pixel clocks in multiples of 1, 2, and 4 using a combination of encoder pulses.

The rotational direction switching means 68 performs control of reversing the rotational direction of the motor 64, based on the pulse count (i.e., the slit count in the encoder 65 detected by the photodiodes 66a and 66b) previously set according to the length in the horizontal scanning direction of the micro array chip 10 input from the outside. The start point of counting a pulse count is represented, for example, by X0 in FIGS. 2A and 3A. Note that the reference position X1 for disposition of the micro array chip 10 is spaced a fixed distance d from the start point X0. The rotational angle αd of the motor 64 corresponding to this distance d corresponds to the pulse count Cd that is counted over the rotational angle αd.

Figure 5A:
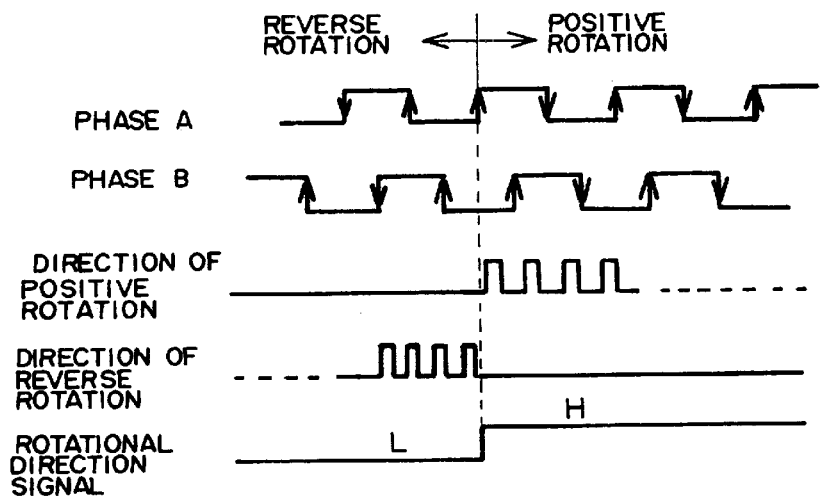
FIG. 5A is a diagram showing rotational angle pulse signals obtained in accordance with rotation of the encoder.
Figure 5B:
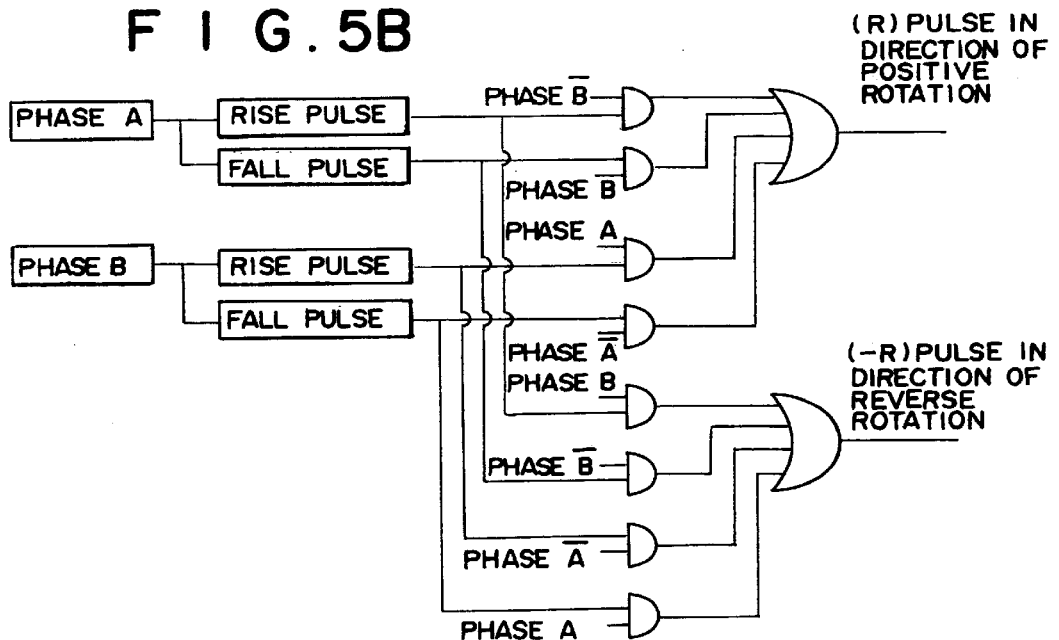
FIG. 5B is a block diagram showing the pulses and edges detected and calculated from the pulse signals shown in FIG. 5A.
Figure 5B:
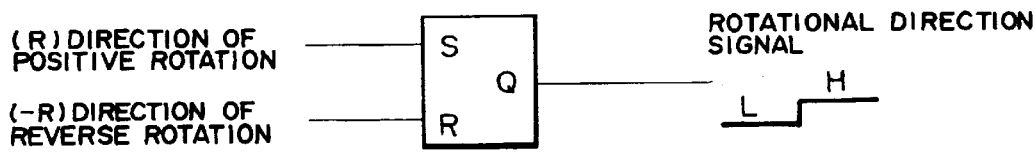

The reading-start-point detection means 70' detects the rotational direction of the motor 64 by taking advantage of a signal waveform having a phase difference of ¼ cycle between the rotational angle pulse signal A of the motor 64 detected by the upper photodiode 65a and the rotational angle pulse signal B of the motor 64 detected by the lower photodiode 65b. More specifically, when the motor 64 rotates in the direction of arrow R, phase A leads phase B by ¼ cycle, as shown in FIG. 5A. When the motor 64 rotates in reverse in the direction of arrow –R. phase B leads phase A by ¼ cycle. Further, in accordance with a block diagram of FIG. 5B showing the pulses and pulse edges detected and calculated from the pulse signals shown in FIG. 5A, a pulse train corresponding to the direction of rotation is generated, whereby a direction signal is formed.

The reading-start-point detection means 70' detects the start point X0, at which the motor 64 switches from reverse rotation to positive rotation, by the above-mentioned operation of detecting the direction of rotation. The reading-start-point detection means 70' also detects X1, which is the start point of reading image information, from the start point X0 by counting a pulse count from the start point X0. When the pulse count reaches the previously set pulse count Cd, the reading-start-point detection means 70' inputs a signal representing the reading start point X1 to the A/D converter 43.

Now, the operation of the image information reader of the first embodiment will be described.

First, laser light L is emitted from the laser light source 30. The emitted laser light L is formed into a laser light beam L by the lens 31 and is reflected upward by the plane mirror 51 of the optical head 50. The reflected light beam L passes through the aperture 52a of the perforated mirror 52 and is focused on the micro array chip 10 through the transparent sample tray 20 by the lens 53. Note that the optical head 50 has initially been stopped by the horizontal scanning means 60 at the initial position where the laser light beam L is focused on the start point X0. Therefore, the laser light beam L has not initially been focused on the micro array chip 10.

On the other hand, the length in the horizontal scanning direction of the micro array chip 10 placed on the sample tray 20 is input to the rotational direction switching means 68. The rotational direction switching means 68 sets the count of the rotational angle pulse signals to be detected by the photodiode 66 (66a, 66b), in accordance with the input length. This setting is performed, for example, by storing a look-up table in which chip lengths and pulse counts correspond to one another and by making reference to this look-up table. Thus, the setting prescribes the timing when rotation of the motor 64 is reversed.

In the first embodiment, the pulse count, which is set according to the length of the micro array chip 10 input to the rotational direction switching means 68, for example, is set to a pulse count Cm corresponding to the length between the start point X0 and a reversal position Xm (see FIG. 3A) which is slightly longer than the length of the micro array chip 10.

Next, the motor 64 rotates in the direction of positive rotation (i.e., the direction of arrow R), whereby the drive pulley 62 coupled to the motor 64 drives the conveyor belt 61 in the direction of arrow X. The optical head 50 fixed integrally to the conveyor belt 61 is also conveyed in the direction of arrow X. The laser light beam L emitted from the optical head 50 is moved from the start point X0 in the direction of arrow X, thereby scanning the micro array chip 10 in the horizontal scanning direction.

The positive rotation of the motor 64, on the other hand, causes the encoder 65 provided coaxially with the drive shaft of the motor 64 to rotate in the direction of arrow R. With this rotation, the photodiodes 66a, 66b output rotational angle pulse signals A and B having a phase difference shown in FIG. 5A. These signals A and B are input to the rotational direction switching means 68 and the reading-start-point detection means 70'. The rotational direction switching means 68 counts the pulse count C in at least either the rotational angle pulse signal A or B until the pulse count C reaches the pulse count Cm corresponding to the previously set reversal position Xm. The reading-start-point detection means 70' detects the start point X0, where the motor 64 switches from its stopped state to positive rotation, based on the phase difference between the rotational angle pulse signals A and B and also counts the pulse count C in at least either the rotational angle pulse signal A or B from the start point X0.

When the horizontal scanning position of the laser light beam L emitted upward from the optical head 50 reaches the reading start position X1 by further rotation of the motor 64, the pulse count C being counted by the reading-start-point detection means 70' reaches the set value Cd and therefore the reading-start-point detection means 70' inputs a signal representing a reading start point to the A/D converter 43. The A/D converter 43 starts the A/D conversion of the image information input from the logarithmic amplifier 42 at the time when this signal representing a reading start point is input.

The laser light beam L emitted upward from the optical head 50 passes the reading start position X1 and then scans the micro array chip 10. When the laser light beam L scans a portion distributing predetermined DNA fragments labeled with a fluorochrome, the fluorochrome is excited by the laser light beam L and emits fluorescence K. The emitted fluorescence K is formed into an almost collimated beam of light by the collimator lens 53 of the optical head 50. The greater part of the light beam K is reflected in the direction of arrow X by the perforated lens 52 and is input to the PMT 40 through the exciting-light cut filter 41. The PMT 40 performs photoelectric conversion with respect to the input fluorescence K and inputs the obtained image information to the logarithmic amplifier 42. The image information amplified by the logarithmic amplifier 42 is input to the A/D converter 43. The A/D converter 43 digitizes the input image information and outputs the digitized information to an external image processor or the like.

The optical head 50 is further moved in the direction of arrow X by the conveyor belt 61. During the movement, the laser light beam L continues to scan the micro array chip 10 and the digital image information is output from the A/D converter 43, by the above-mentioned operation. When the scanning position of the laser light beam L reaches the reversal position Xm (see FIG. 3A), the pulse count c input to the rotational direction switching means 68 reaches the previously set pulse count Cm and therefore the rotational direction switching means 68 switches the rotational direction of the motor 64 from positive rotation to reverse rotation (i.e., rotation in the direction of arrow –R). With this reverse rotation, the optical head 50 is returned in the direction of arrow –X. Simultaneously, the emission of the laser light L from the light source 30 is stopped. In addition, the reverse rotation of the motor 64 is detected based on the phase difference between two rotational angle pulse signals detected with the photodiodes 66a, 66b, by the reading-start-point detection means 70'. The reading-start-point detection means 70' inputs a reading stop signal to the A/D converter 43, which in turn outputs no digital image information.

On the other hand, the rotational angle pulse signals detected by the photodiodes 66a, 66b are input to the rotational direction switching means 68, which in turn counts the pulse count C in the rotational angle pulse signal from the reversal of the motor 64. While the optical head 50 is being moved in the direction of arrow –X by the reverse rotation of the motor 64, the vertical scanning means 80 scans the sample tray 20 in the direction of arrow Y.

When the pulse count C in the rotational angle pulse signal input to the rotational direction switching means 68 reaches the previously set pulse count Cm, the optical head 50 is returned to the position where the laser light beam L therefrom is emitted to the position X0. The motor 64 is again rotated in reverse and therefore the optical head 50 moves in the direction of arrow X. Simultaneously, the light source 30 emits laser light L. The reading-start-point detection means 70' detects the reversal of the rotational direction of the motor 64, based on the phase difference between two rotational angle pulse signals detected by the photodiodes 66a, 66b. The pulse count C in either of the rotational angle pulse signals, input from the photodiodes 66a, 66b, is again counted from the reversal. When the pulse count C being counted reaches the set value Cd, the reading-start-point detection means 70' inputs a reading start signal to the A/D converter 43. As with the aforementioned operation, the A/D converter 43 starts the A/D conversion of the image information input from the logarithmic amplifier 42 at the time when the reading start signal is input.

By reiterating the foregoing operation, digital image information about an image of a distribution of fluorescence K can be obtained over the entire surface of the micro array chip 10.

According to the image information reader of the first embodiment, as described above, the reading start point X1 is obtained by taking advantage of the signal from the existing encoder 65 hitherto being used for keeping the range of horizontal scanning (X0~Xm) constant. Thus, there is no need to provide an additional start-point sensor or the like in the optical path of the laser light beam L or the horizontal scanning line in order to detect the reading start point X1, and consequently the construction can be simplified. When a start point sensor is additionally provided, there is a need to ensure space for attaching the start point sensor, and because such space is not needed, this is also effective in reducing the size of the image information reader.

While the image information reader of the first embodiment has obtained digital image information by emitting laser light only when the optical head is moved in one direction, the reading-start-point detecting method and the image information read of the present invention are not to be limited to this embodiment but are applicable to bi-directional reading that performs reading in the returning direction as well. Particularly, in image information readers capable of reading out image information from various kinds of micro array chips differing from one another in length in the horizontal scanning direction, the effect is more noticeable. More specifically, the reading start point X1 in the going direction (X direction) is always constant regardless of a length difference in the horizontal scanning direction, but the reading start point in the returning direction (-X direction) varies depending on the length in the horizontal scanning direction. The aforementioned conventional image information readers, therefore, need to provide start point sensors at different reading start points. The start point detecting method and the image information reader of the present invention, on the other hand, detect when the rotational direction of rotary drive means such as a motor is reversed, and obtain a reading start point, based on the pulse count input with the reversal as a reference. Thus, there is no need to provide a start point sensor for each different reading start point.

Although the image information reader of the first embodiment has been applied to the micro array chip that is a sample to be read, the reading-start-point detecting method and the image information reader of the present invention are not to be limited to the micro array chip. For example, they are applicable to various samples, such as gel distributing a specific organism-oriented matter labeled with a fluorochrome, and a membrane filter, a micro-titre plate and the like obtained by transferring this gel.

A second embodiment of the scanner of the present invention that carries out the scanning-start-point detecting method will hereinafter be described with reference to the drawings.

Figure 1B:
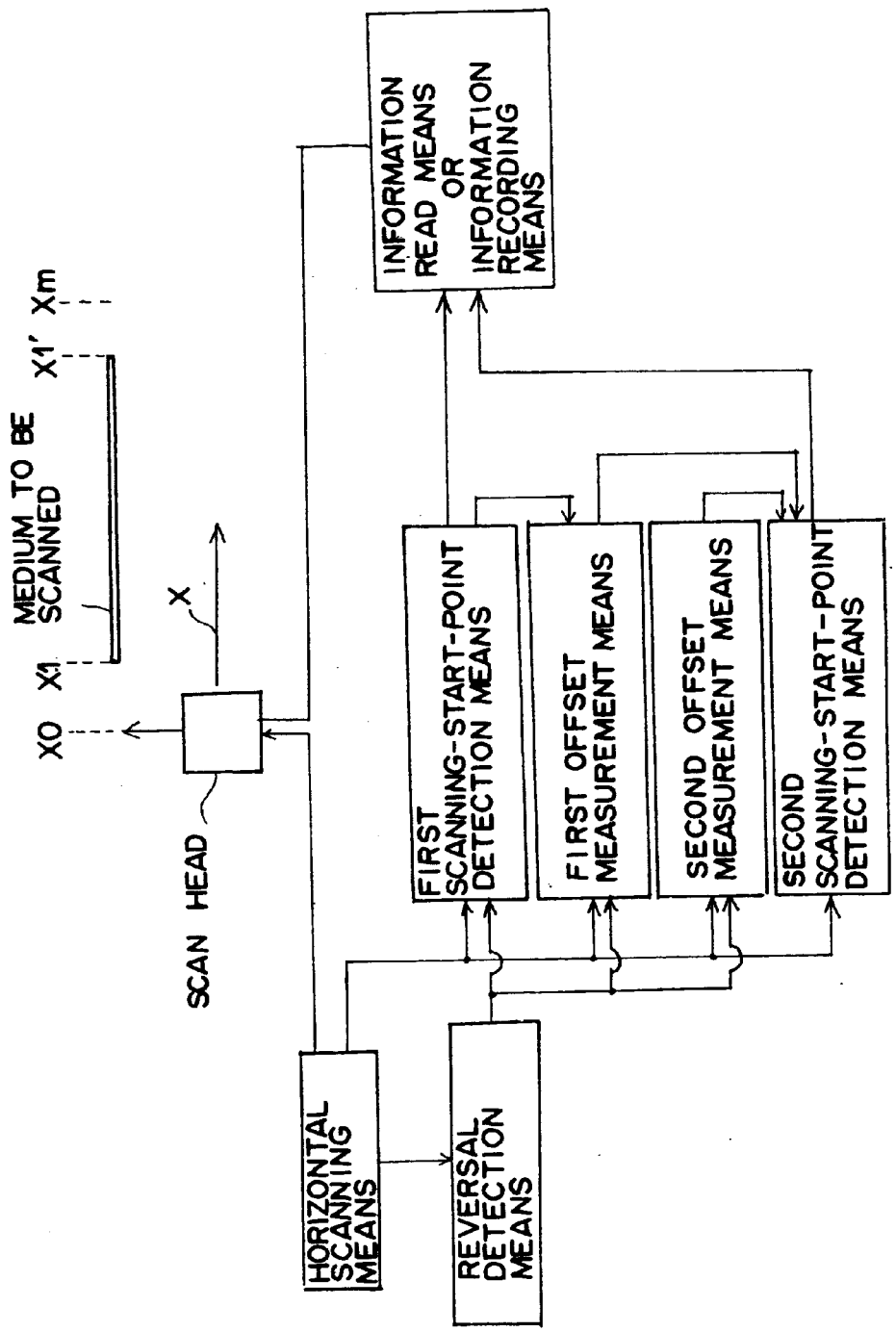
FIG. 1B is a block diagram showing a second embodiment of the scanner of the present invention.

FIG. 1B shows the second embodiment of the scanner of the present invention. The scanner shown in the figure detects a reading start point which starts reading information in the direction of horizontal scanning or a recording start point which starts recording information in the direction of horizontal scanning, by relatively moving a scan head, which reads out information from a predetermined medium to be scanned or records information on the medium, in the going and returning directions by horizontal scanning means so that the scan head can reiteratively perform horizontal scanning in a fixed direction with respect to the medium. The scanner includes: (1) reversal detection means which detects that the direction of the scan head being moved by the horizontal scanning means has been reversed from the going direction (direction of arrow X) to the returning direction (direction opposite from the arrow X); (2) first scanning-start-point detection means which detects a scanning start point in the going direction of the horizontal scanning which is performed by the horizontal scanning means; (3) first offset measurement means which measures a moved distance in the going direction of the scan head between a scanning end point which ends scanning, set according to the length in the horizontal scanning direction of the medium, and reversal of the horizontal scanning means; (4) second offset measurement means which measures a moved distance in the returning direction of the scan head from the reversal detected by the reversal detection means; and (5) second scanning-start-point detection means which detects a horizontal scanning position, where the moved distance in the returning direction detected by the second offset measurement means coincides with the moved distance in the going direction detected by the first offset measurement means, as a scanning start point in the returning direction.

Now, the operation of the scanner of the second embodiment will be described.

First, the horizontal scanning means moves the scan head from a stop position X0 in the direction of arrow X (i.e., the going direction). The horizontal scanning means inputs a signal corresponding to the moved distance of the scan head (e.g., an encoder pulse signal) to the first and second scanning-start-point detection means and the first and second offset detection means. The first scanning-start-point detection means detects an encoder pulse count corresponding to a distance from the stop position X to a scanning start position X1 in the going direction, thereby detecting a scanning start point in the returning direction. The first scanning-start-point detection means inputs instructions to start scanning to either information read means which reads out information from a medium to be scanned or information recording means which records information on a medium to be scanned. The information read means starts reading information from the medium through the scan head, or the information recording means starts recording information on the medium through the scan head.

On the other hand, when scanning in the going direction advances and reaches a scanning end point X1', instructions to end scanning are input from the first scanning-start-point detection means to the information read means or the information recording means, and the information read means or the information recording means ends reading or recording. The instructions to end scanning are also input from the first scanning-start-point detection means to the first offset measurement means, which in turn starts counting the pulses in an encoder pulse signal until the reversal detection means detects the reversal of the scan head from the going direction to the returning direction.

When the scan head reaches the reversal position Xm under control of the horizontal scanning means, the scan head reverses the moving direction and starts moving in the direction (returning direction) opposite from the direction of arrow X.

The reversing operation performed by the horizontal scanning means is detected by the reversal detection means. The reversal detection means inputs the result of detection to the first and second offset measurement means. The first offset measurement means stops counting, started from the reading end position X1', at the time when the result of detection from the reversal detection means is input, and then inputs the pulse count to the second scanning-start-point detection means.

The second offset measurement means, on the other hand, starts counting encoder pulses from the reversal position Xm at the timing when the detection result from the reversal detection means is input, and then inputs the pulse count to the second scanning-start-point means.

When the scanning in the returning direction by the scan head advances and reaches the scanning end point X1' in the returning direction, the pulse count being counted by the second offset measurement means coincides with the pulse count counted by the first offset measurement means. The coincidence between the pulse counts is detected by the second scanning-start-point detection means. The second scanning-start-point detection means inputs instructions to start scanning in the returning direction to the information read means or the information recording means.

Upon input of the instructions, the information read means starts reading information from the medium through the scan head, or the information recording means starts recording information on the medium through the scan head.

On the other hand, when scanning in the returning direction advances and reaches the scanning end point X1, instructions to end scanning are input from the second scanning-start-point detection means to the information read means or the information recording means. The information read means or the information recording means then end reading or recording.

When the scanning in the returning direction by the scan head advances and reaches the reversal position X0, the horizontal scanning means reverses the moving direction of the scan head in the direction of arrow X (i.e., the going direction) and then reiterates the above-mentioned operation.

According to the scanner of the first embodiment, as described above, the distance of the scan head, moved between the scanning end point in the going direction of horizontal scanning and the reversal of the horizontal scanning, is obtained. The moved point of the scan head, moved from the reversal of the horizontal scanning means in the returning direction by the obtained moved distance, is regarded as the scanning start point in the returning direction, whereby the scanning end point in the going direction coincides with the scanning start point in the returning direction. This renders it possible to read out or record information without any pixel difference between the going direction and the returning direction. In addition, even when there is a length difference in the horizontal scanning direction between mediums to be scanned, there is no need to provide a component, such as a reference section which becomes a different scanning start point reference in the returning direction, for each length.

Figure 2C:
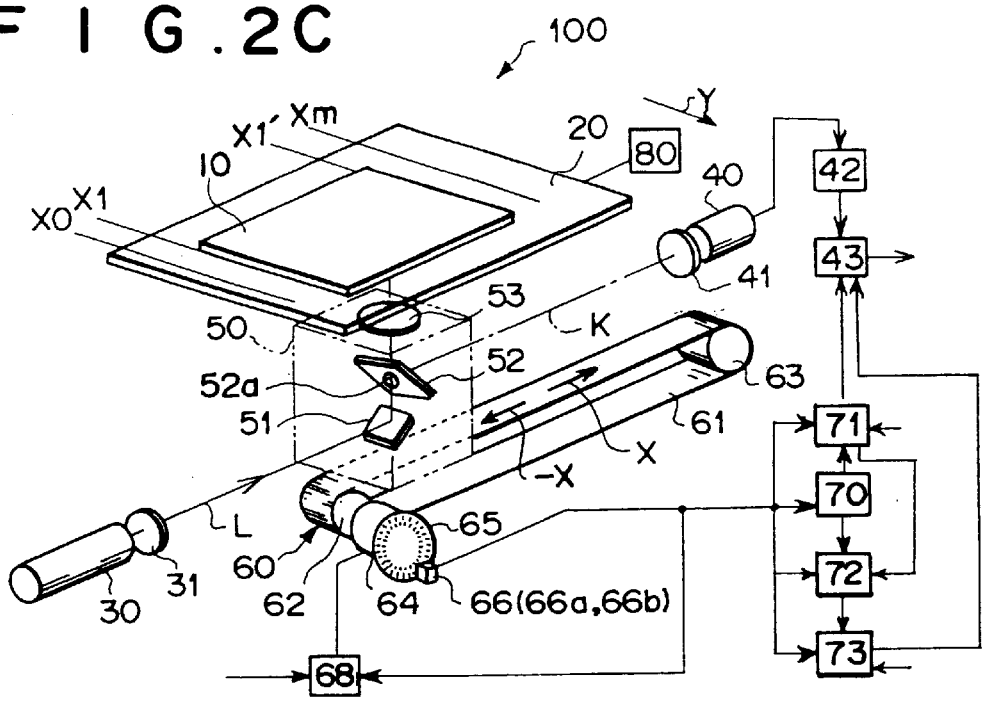
FIG. 2C is a perspective view of a second embodiment of the image information reader of the present invention.
Figure 2D:
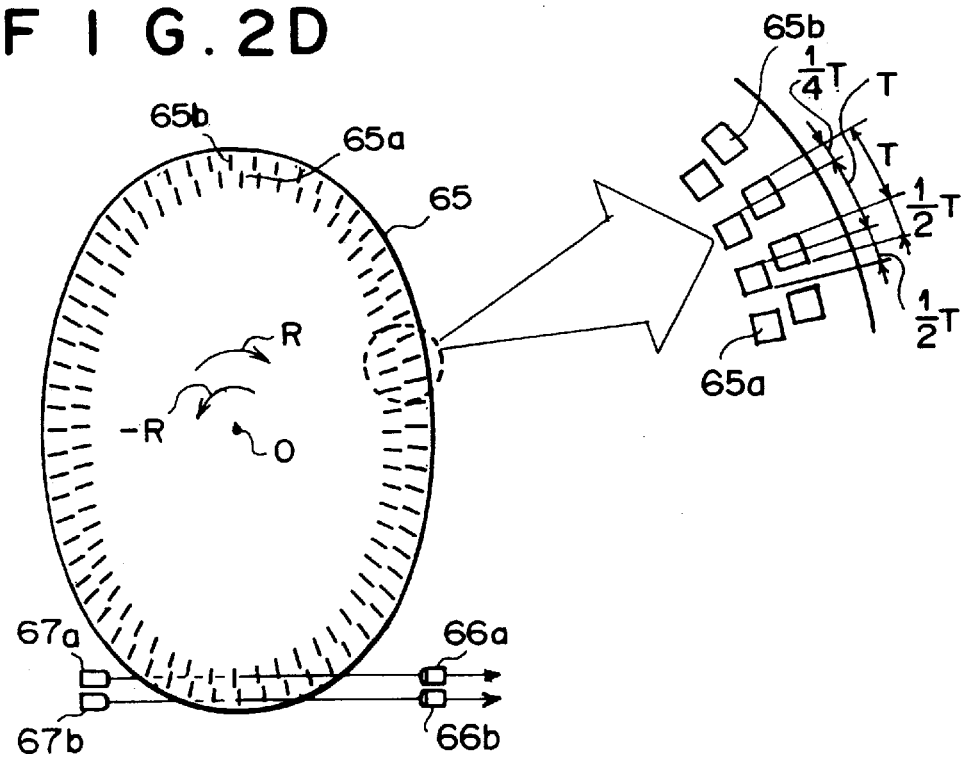
FIG. 2D shows an enlarged view of the encoder and vicinity of the image information reader shown in FIG. 2C.
Figure 3B:
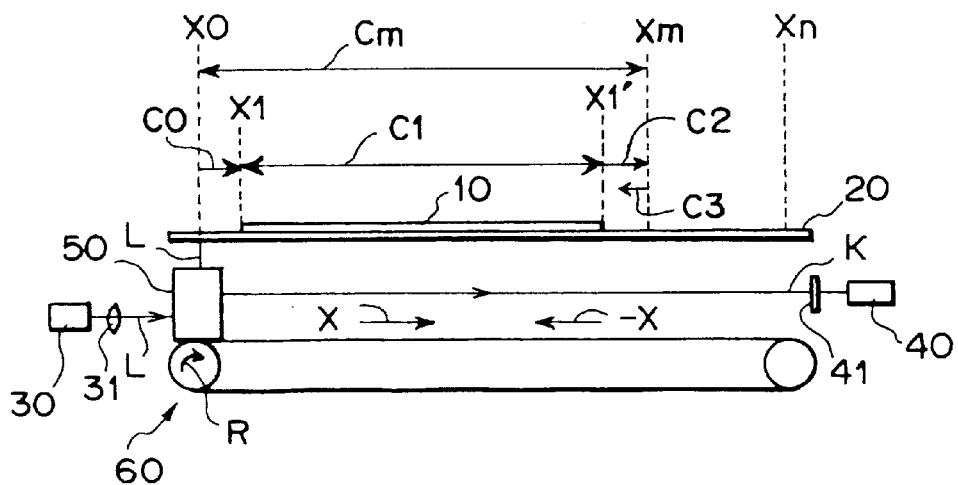
FIG. 3B is a diagram for describing the operation of the image information reader shown in FIG. 2C.

FIG. 2C shows a second embodiment of the image information reader of the present invention and FIG. 2D shows the encoder and vicinity of the image information reader shown in FIG. 2C. FIG. 3B is used to describe the operation of the image information reader shown in FIG. 2C and FIG. 4 shows a sample (e.g., a micro array chip) that is read out by the image information reader shown in FIG. 2C.

The image information reader 100' shown in FIG. 2A comprises: (1) a transparent sample tray 20 on which a micro array chip 10, such as that shown in FIG. 4, is placed so that the edge of the chip 10 coincides with a predetermined reference position X1, the chip 10 including a predetermined hybridized DNA (an example of organism-originated matters) labeled with a fluorochrome; (2) a laser light source 30 which emits laser light L having a wavelength band that excites the above-mentioned fluorochrome; (3) a lens 31 which forms the laser light L emitted from the light source 30 into a beam of light; (4) a photomultiplier tube (hereinafter referred to as a PMT) 40 which photoelectrically detects fluorescence K emitted from the fluorochrome of the micro array chip 10 excited with the laser light beam L; (5) an optical head 50 which emits the laser light beam L to the micro array chip 10 placed on the sample tray 20 and guides fluorescence K, emitted from the micro array chip 10 irradiated with the laser light beam L, to the PMT 40; (6) a laser-light cut filter 41 disposed in the optical path between the optical head 50 and the PMT 40; (7) horizontal scanning means 60 which reiteratively moves the optical head 50 at uniform velocity in the direction of arrow X (a going direction) and the direction of arrow −X (the opposite direction from the direction of arrow X; a returning direction); (8) vertical scanning means 80 which moves the micro array chip 10 and the sample tray 20 in the direction of arrow Y substantially perpendicular to the direction of arrow X; (9) reversal detection means 70 which detects the rotational direction of a motor 64 constituting part of the horizontal scanning means 60 and detects that the horizontal scanning direction of the scan head 50 has been reversed from the X direction to the −X direction; (10) first reading-start-point detection means 71 which detects a reading start point that starts reading fluorescence K in the horizontal scanning of X direction which is performed by the horizontal scanning means 60; (11) offset measurement means 72 which measures a moved distance in the X direction of the scan head 50 between a reading end point X1' which ends reading fluorescence K, set according to the length in the X direction of the micro array chip 10, and the reversal (position Xm) of the horizontal scanning means 60, the offset measurement means 72 also detecting a moved distance in the −X direction of the optical head 50 from the reversal (position Xm) of the optical head 50 detected by the reversal detection means 70, and outputting these results of detection to second reading-start-point detection means 73 (described below) in real time; (12) second reading-start-point detection means 73 which detects a moved position, where the moved distance in the −X direction input from the offset measurement means 72 coincides with the moved distance in the X direction, as a reading start point X1' in the −X direction; (13) rotational direction switching means 68 which performs control for reversing the rotational direction of the motor 64, based on the rotational angle of the motor 64; (14) an amplifier 42 which logarithmically amplifies a detection signal detected by the PMT 40; and (15) an A/D converter 43 which converts the amplified detection signal to a digital signal at the time when the reading start points X1 and X1' are detected by the first reading-start-point detection means 71 and the second reading-start-point detection means 73.

Here, the light source 30 is disposed such that the laser light L therefrom is emitted in a direction along the direction of arrow X, and the PMT 40 is disposed such that it detects fluorescence K incident along the direction of arrow X.

The optical head 50 includes a plane mirror 51, a perforated mirror 52, and a collimator lens 53. The plane mirror 51 reflects the laser light beam L, traveling in the direction of arrow X, in a direction perpendicular to the micro array chip 10 (which is an upward direction in FIG. 2C). The perforated mirror 52 is formed with an aperture 52a that the laser light beam L reflected by the plane mirror 51 passes through. This perforated mirror 52 reflects the greater part of the fluorescence K, emitted downward from the lower surface of the micro array chip 10, in the direction of arrow X so that the reflected fluorescence K is incident on the PMT 40. The collimator lens 53 forms the fluorescence K emitted from the lower surface of the micro array chip 10 into an almost collimated beam of light. The plane mirror 51, the perforated mirror 52, and the lens 53 are constructed integrally with one another.

The laser-light cut filter 41 is a filter with a band limited so as to permit the passage of fluorescence K but prevent the passage of laser light L, in order to prevent the incidence of the laser light L on the PMT 40 even when part of the laser light L, scattered and reflected at the micro array chip 10 and the sample tray 20, travels toward the PMT 40 along with fluorescence K.

The horizontal scanning means 60 includes (1) a motor 64; (2) a drive pulley 62 that is driven to rotate by this motor 64; (3) a conveyor belt 61, looped between the drive pulley 62 and an idle pulley 63, for integrally moving the optical head 50 in the direction of arrow X in accordance with the rotation in the direction of arrow R (clockwise direction) of the drive pulley 62 and also in the direction of arrow –X in accordance with the rotation in the direction of arrow –R (counterclockwise direction) of the drive pulley 62; (4) an encoder 65 (see FIG. 2D) mounted at its center on the drive shaft of the motor 64; and (5) light-emitting diodes 67a, 67b and photodiodes 66a, 66b which generate rotational angle pulse signals by rotation of the encoder 65 and detect the generated rotational angle pulse signals.

The encoder 65, as shown in FIG. 2D, is provided with two rows of inner and outer slits 65a, 65b, which are disposed at different radial positions from the center 0 of the encoder 65 in the circumferential direction of the encoder 65. The inner circumferential slit row 65a and the outer circumferential slit row 65b are both formed at equal intervals over the entire circumference of the encoder 65. There is a phase difference of ¼ cycle between the inner circumferential slit row 65a and the outer circumferential slit row 65b.

The upper light-emitting diode 67a and the upper photodiode 66a correspond to the inner circumferential slit row 65a of the encoder 65, while the lower light-emitting diode 67b and the lower photodiode 66b correspond to the outer circumferential slit row 65b. With this arrangement, a single pulse (high level) is detected every time the slit of each slit row passes through the optical path between the light-emitting diode and the photodiode. Note that the scanner of the second embodiment generates pixel clocks in multiples of 1, 2, and 4 using a combination of encoder pulses.

The rotational direction switching means 68 performs control for reversing the rotational direction of the motor 64, based on the pulse count (i.e., the slit count in the encoder 65 detected by the photodiodes 66a and 66b) previously set according to the length in the horizontal scanning direction of the micro array chip 10 input from the outside. The start point of counting a pulse count is represented, for example, by X0 in FIGS. 2C and 3B.

In FIG. 3B the reference position X1 for disposition of the micro array chip 10 is spaced a fixed distance d from the start point X0. The rotational angle α of the motor 64 corresponding to this distance corresponds to the pulse count C0 that is counted over the rotational angle. The pulse count C1 corresponding to the length in the X direction (|X1'–X1|) of the micro array chip 10 is previously calculated, these pulse counts C0 and C1 being stored in a host computer.

The reversal detection means 70 detects the rotational direction of the motor 64 by taking advantage of a signal waveform having a phase difference of ¼ cycle between the rotational angle pulse signal A of the motor 64 detected by the upper photodiode 65a and the rotational angle pulse signal B of the motor 64 detected by the lower photodiode 65b. More specifically, when the motor 64 rotates in the direction of arrow R, phase A leads phase B by ¼ cycle, as shown in FIG. 5A. When the motor 64 rotates in reverse in the direction of arrow –R, phase B leads phase A by ¼ cycle. As shown in the block diagram of FIG. 5B showing the pulses and pulse edges detected and calculated from the pulse signals shown in FIG. 5A, a pulse train corresponding to the direction of rotation is generated, whereby a direction signal is formed.

The first reading-start-point detection means 71 detects the reading start point X1, based on the pulse count from the photodiode 66a (or 66b) corresponding to a distance (=X1–X0) that the optical head 50 moves from the position X0 (i.e., an initial position and a position which reverses the optical head 50 from the X direction to the –X direction) in the X direction. At this time, the position where the pulse count from the photodiode 66a (or 66b) coincides with the pulse count C0 input from the above-mentioned host computer (not shown) is detected as the reading start point X1.

When the first reading-start-point detection means 71 detects the above-mentioned position as the reading start point X1, the detection means 71 inputs this result of detection to the A/D converter 43, which in turn starts A/D conversion at the time when the detection result is input. Furthermore, the pulse count C1 corresponding to the length of the micro array chip 10 is input from the host computer to the first reading-start-point detection means 71. The first reading-start-point detection means 71 detects the point, where the pulse count input from the photodiode 65a after detection of the reading start point X1 reaches C1, as the reading end point X1'. This result of detection is input to the A/D converter 43 and the offset measurement means 72. The A/D converter 43 ends A/D conversion at the time when the detection result is input.

The offset measurement means 72 starts counting the pulse count input from the photodiode 66a from 0 when the detection result of the reading end point X1' is input from the first reading-start-point detection means 71 and stops counting when the reversal detection means 70 detects the reversal of the motor 64 (reversal from position rotation). The pulse count C2 is input to the second reading-start-point detection means 73. Simultaneously, a pulse count C3 from the reversal of the motor 64 detected by the reversal detection means 70 is input to the second reading-start-point detection means 73 in real time. Note that the pulse count C2 corresponds to the offset distance from the reading end point X1' (which corresponds to the rear end of the micro array chip 10) to the reversal position Xm.

The second reading-start-point detection means 73 detects the scanning position, where the pulse count C3 after reversal of the motor 64 input from the offset measurement means 72 coincides with the pulse count C2 before reversal of the motor 64, as the reading start point X1' in the returning direction (which coincides with the reading end point in the going direction). The result of detection is input to the A/D converter 43, which in turn starts A/D conversion at the time when the detection result is input. Furthermore, the pulse count C1 corresponding to the length of the micro array chip 10 is input from the host computer to the second reading-start-point detection means 73. The second reading-start-point detection means 73 detects the point, where the pulse count input from the photodiode 65a after the detection of the reading start point X1 reaches C1, as the reading end point X1'. This result of detection is input to the A/D converter 43 and the offset measurement means 72. The A/D converter 43 ends A/D conversion at the time when the detection result is input.

Now, the operation of the image information reader 100' of the second embodiment will be described.

First, laser light L is emitted from the laser light source 30. The emitted laser light L is formed into a laser light beam L by the lens 31 and is reflected upward by the plane mirror 51 of the optical head 50. The reflected light beam L passes through the aperture 52a of the perforated mirror 52 and is focused on the micro array chip 10 through the transparent sample tray 20 by the lens 53. Note that the optical head 50 has initially been stopped by the horizontal scanning means 60 at the initial position where the laser light beam L is focused on the start point X0. Therefore, the laser light beam L has not initially been focused on the micro array chip 10.

On the other hand, the length in the horizontal scanning direction of the micro array chip 10 placed on the sample tray 20 is input to the rotational direction switching means 68. The rotational direction switching means 68 sets the count of the rotational angle pulse signals to be detected by the photodiode 66 (66a, 66b), in accordance with the input length. This setting is performed, for example, by storing a look-up table in which lengths and counts correspond to one another and by making reference to this look-up table. Thus, the setting prescribes the timing at which rotation of the motor 64 is reversed.

In the second embodiment, the pulse count, which is set according to the length of the micro array chip 10 input to the rotational direction switching means 68, for example, is set to a pulse count cm corresponding to the length between the start point X0 and a reversal position Xm (see FIG. 3B) which is slightly longer than the length of the micro array chip 10.

Next, the motor 64 rotates in the direction of positive rotation (i.e., the direction of arrow R), whereby the drive pulley 62 coupled to the motor 64 drives the conveyor belt 61 in the direction of arrow X. The optical head 50 integrally fixed to the conveyor belt 61 is also conveyed in the direction of arrow X. The laser light beam L emitted from the optical head 50 is moved from the start point X0 in the direction of arrow X, thereby scanning the micro array chip 10 in the horizontal scanning direction.

The positive rotation of the motor 64, on the other hand, causes the encoder 65 provided coaxially with the drive shaft of the motor 64 to rotate in the direction of arrow R. With this rotation, the photodiodes 66a, 66b output rotational angle pulse signals A and B having a phase difference shown in FIG. 5A. These signals A and B are input to the rotational direction switching means 68, the reversal detection means 70, the first and second reading-start-point detection means 71, 73 and the offset measurement means 72.

The rotational direction switching means 68 counts the pulse count C in at least either the rotational angle pulse signal A or B until the pulse count C reaches the pulse count Cm corresponding to the previously set reversal position Xm.

The reversal detection means 70 detects the start point X0, where the motor 64 switches from its stopped state to positive rotation, based on the phase difference between the rotational angle pulse signals A and B. This result of detection is input to the first reading-start-point detection means 71, which starts counting the rotational angle pulse signal from the time that the detection result is input.

When the horizontal scanning position of the laser light beam L emitted upward from the optical head 50 reaches the reading start position X1 by further rotation of the motor 64, the pulse count C being counted by the first reading-start-point detection means 71 reaches the set value C0 and therefore the first reading-start-point detection means 71 inputs a signal representing a reading start point to the A/D converter 43 and also resets the pulse count to 0 and starts counting again. The A/D converter 43 starts the A/D conversion of the image information input from the logarithmic amplifier 42 at the time when the signal representing a reading start point is input.

The laser light beam L emitted upward from the optical head 50 passes the reading start position X1 and then scans the micro array chip 10. When the laser light beam L scans a portion distributing predetermined DNA fragments labeled with a fluorochrome, the fluorochrome is excited by the laser light beam L and emits fluorescence K. The emitted fluorescence K is formed into an almost collimated beam of light by the collimator lens 53 of the optical head 50. The greater part of the light beam K is reflected in the direction of arrow X by the perforated lens 52 and is input to the PMT 40 through the exciting-light cut filter 41. The PMT 40 performs photoelectric conversion with respect to the input fluorescence K and inputs the obtained image information to the logarithmic amplifier 42. The image information amplified by the logarithmic amplifier 42 is input to the A/D converter 43. The A/D converter 43 digitizes the input image information and outputs the digitized information to an external image processor or the like.

The optical head 50 is further moved in the direction of arrow X by the conveyor belt 61. During the movement, the laser light beam L continues to scan the micro array chip 10 and the digital image information is output from the A/D converter 43, by the above-mentioned operation. When the scanning position of the laser light beam L reaches the rear end position X1' in the X direction of the micro array chip 10, the pulse count from the reading start point X1 reaches the value C1 input from the host computer. In this way, the first reading-start-point detection means 71 inputs a reading end signal to the A/D converter 43 and the offset measurement means 72. The A/D converter 43 stops the A/D conversion of a signal input from the amplifier 42 and ends the reading in the X direction. On the other hand, the offset measurement means 72 starts counting a pulse count in the rotational angle pulse signal from the timing that the first reading-start-point detection means 71 inputs the reading end signal.

When the scanning in the X direction by the laser light beam L further advances and the scanning position reaches the reversal position Xm, the pulse count detected by the rotational direction switching means 68 reaches the previously set Cm. The rotational direction switching means 68 switches the rotational direction of the motor 64 from the direction of arrow R to the direction of arrow −R. With this operation, the moving direction of the optical head 50 is also reversed from the direction of arrow X to the direction of arrow −X. The vertical scanning means 80 scans the sample tray 20 in the direction of arrow Y.

The reversal detection means 70 detects by the aforementioned operation that the rotational direction of the motor 64 has been inverted. This result of detection is input to the offset measurement means 72. In response to the input of the reversal detection, the offset measurement means 72 stops counting pulses and inputs the pulse count C2 at that time to the second reading-start-point detection means 73. Simultaneously, the offset measurement means 72 resets the pulse count to 0 and starts counting again. The pulse count started is input to the second reading-start-point detection means 73.

When the rotational direction of the motor 64 is reversed and the horizontal scanning position of the laser light beam L emitted upward from the optical head 50 being moved in the −X direction reaches the reading end point X1' of the horizontal scanning in the X direction, the pulse count C3 input to the second reading-start-point detection means 73 coincides with the pulse count C2 corresponding to an offset value in the horizontal scanning in the X direction. The scanning position X1' is detected as the reading start point at the horizontal scanning in the −X direction (which is the returning direction). This result of detection is input to the A/D converter 43. Simultaneously, the input pulse count is reset to 0 and counting is restarted. At the time that the detection result of the reading start point X1' is input, the A/D converter 43 digitizes the input image information and outputs it to an external image processor or the like.

The optical head 50 is further moved in the direction of arrow −X by the conveyor belt 61. During the movement, the laser light beam L continues to scan the micro array chip 10 and the digital image information is output from the A/D converter 43, by the above-mentioned operation. When the scanning position of the laser light beam L reaches the end position X1 in the −X direction of the micro array chip 10 (which is the reading start point in the X direction), the pulse count from the reading start point X1' reaches the value C1 input from the host computer. In this way, the second reading-start-point detection means 73 inputs a reading end signal to the A/D converter 43, which in turn stops the A/D conversion of a signal input from the amplifier 42 and ends the reading in the −X direction.

When the scanning in the X direction by the laser light beam L further advances and the scanning position reaches the reversal position X0, the pulse count detected by the rotational direction switching means 68 reaches the previously set value Cm. The rotational direction switching means 68 switches the rotational direction of the motor 64 from the direction of arrow −R to the direction of arrow R. With this operation, the moving direction of the optical head 50 is also reversed from the direction of arrow −X to the direction of arrow X. At this time, the rotational direction switching means 68 resets the pulse count to 0.

The vertical scanning means 80, on the other hand, scans the sample tray 20 in the direction of arrow Y.

With the foregoing operation, a single horizontal scan in the going and returning directions ends. By reiterating this operation, the laser light beam L scans the entire surface of the micro array chip 10 and digitized image information related to an image of a distribution of fluorescence K can be acquired.

According to the image information reader of the second embodiment, as described above, a pulse count corresponding to the moved distance of the optical head 50 between the reading end point X1' in the going direction (X direction of the horizontal scanning and the reversal (Xm) of the horizontal scanning is obtained. The point X1, obtained when the horizontal scanning means 60 moves from the reversal thereof in the returning direction by a distance corresponding to the obtained pulse count, is regarded as the reading start point in the returning direction, whereby the reading end point in the going direction coincides with the reading start point in the returning direction. In this way, image information having no pixel difference between the going and returning directions can be acquired, and reading can be performed in both directions, the going and returning directions, so that reading can be performed at a high speed.

In addition, the image information reader of the second embodiment is capable of reading an image of a distribution of fluorescence K from micro array chips differing in length in the horizontal scanning direction. When the horizontal scanning range of the optical head 50 is in a range of X0 to Xn (see FIG. 3) longer than the aforementioned range of 0 to Xm, for example, the pulse count Cn corresponding to the scanning position Xn of reversing the rotational direction of the motor 64 is input from the host computer to the rotational direction switching means 68. The pulse count C1 corresponding to the length of the micro array chip is input to the first and second reading-start-point detection means 71, 73. Thus, the reading end point in the going direction and the reading start end in the returning direction will always coincide with each other even if there are various kinds of micro array chips each having a different length. Therefore, image information can be acquired accurately at a high speed without any pixel difference.

While the image information reader of the second embodiment has been applied to the micro array chip that is a sample to be read, the image information read method and the image information reader of the present invention are not to be limited to the micro array chip. For instance, they are applicable to various samples, such as gel distributing a specific organism-oriented matter labeled with a fluorochrome, and a membrane filter, a micro-titre plate and the like obtained by transferring this gel.

While the first reading-start-point detection means 71 in the second embodiment obtains the reading start point X1 in the going direction by counting pulses generated from the encoder 61, the present invention is not limited to the detection means 71. The detection of the reading start point in the going direction may be performed by employing an external passage sensor or the like differing from the horizontal scanning means.

The image information reader of the second embodiment has been described on the assumption that, between the drive pulley 62 and the conveyor belt 61 constituting the horizontal scanning means 60, there is no slip in the practical range at the time of the reversal of the motor 64. However, there are cases where a slip is great enough to affect a pixel difference between the going and returning directions. In such a case, the pulse count corresponding to a slip (length) at the time of reversal is previously calculated and the second reading-start-point detection means makes a correction by the amount of the previously obtained pulse count so that the reading start point in the returning direction coincides with the reading end point in the going direction, whereby a reading start point in the returning direction may be detected. Instead of directly correcting the pulse count, a correction may be made by a delay circuit which delays the detecting time by the time required to count the pulse count.

Figure 6:
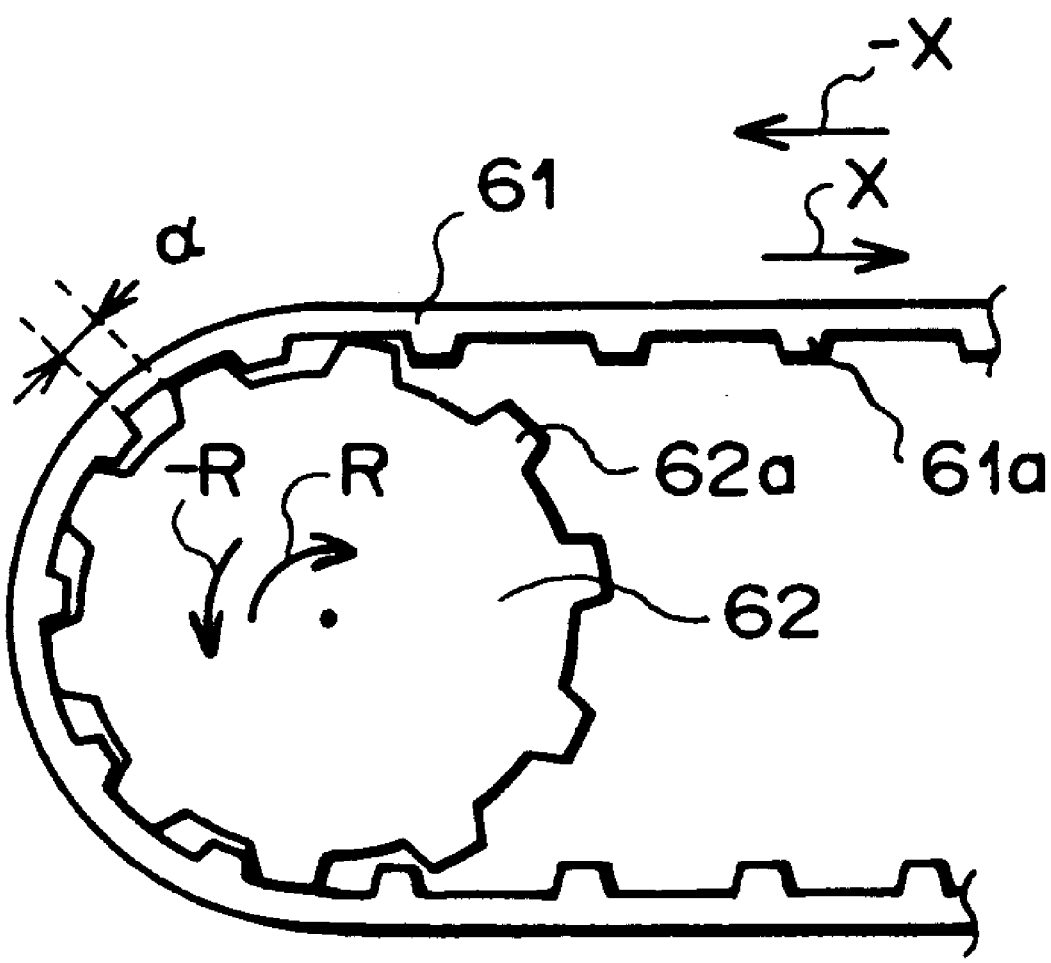
FIG. 6 is a diagram showing how backlash affects horizontal scanning.

The above-mentioned correction by the second reading-start-point detection means is also applied to the case of correcting backlash between the tooth 62a of the drive pulley 62 and the engaging protrusion 61a of the conveyor belt, as shown in FIG. 6, for example.

That is, when the rotation of the motor 63 is reversed from positive rotation, the reversal of the moving direction of the conveyor belt 61 is delayed by the amount of backlash α from the reversal of the rotational direction of the drive pulley 62, and consequently, this backlash α results in a free running distance.

Hence, a pulse count corresponding to the backlash a is previously measured and the second reading-start-point detection means corrects the pulse count in the returning direction, measured with the offset measurement means, by the amount of a pulse count corresponding to the previously measured pulse count. Alternatively, the second reading-start-point detection means makes a correction by delaying detecting time by the amount of time corresponding to the pulse count. In this manner, the reading start point in the returning direction can be detected.

Although, in the above-mentioned second embodiment, the scanner of the present invention is applied to the image information reader, it is a matter of course that the scanner of the present invention is applicable to a recorder such as a printer or the like which reiteratively performs horizontal scanning.

What is claimed is:

1. A method of detecting a reading start point which starts reading information in a horizontal scanning direction or a recording start point which starts recording information in said horizontal scanning direction, by relatively moving a predetermined medium to be scanned and/or a scan head, which reads said information from said medium or records said information on said medium, by horizontal scanning means so that said scan head can reiteratively perform horizontal scanning in a fixed direction with respect to said medium, said method comprising the steps of:

generating two rotational angle pulse signals having a phase difference which varies according to a rotational direction of a rotary drive means provided in said horizontal scanning means;

causing said horizontal scanning direction to depend on the rotational direction of said rotary drive means;

detecting reversal of the rotational direction of said rotary drive means, based on said phase difference between said two rotational angle pulse signals;

detecting said rotational angle pulse signals from the reversal of said rotational direction; and detecting said scanning start point, based on the detected rotational angle pulse signals.

2. The method as set forth in claim 1, wherein timing at which the rotational direction of said rotary drive means switches is changed according to a length in said horizontal scanning direction of said medium.

3. A method of reading out image information from a predetermined sample, using an image information reader comprising an exciting light source for emitting exciting light, an optical head for emitting said exciting light to said sample, horizontal scanning means for relatively moving said optical head and/or said sample so that said exciting light can repeatedly perform horizontal scanning by a predetermined length in a fixed direction with respect to said sample, vertical scanning means for relatively moving said optical head and/or said sample in direction substantially perpendicular to said horizontal scanning direction so that said exciting light can perform vertical scanning with respect to said sample, and photoelectric read means for photoelectrically reading out luminescence emitted from said sample irradiated with said exciting light by said relative scanning, said method comprising the steps of:

generating two rotational angle pulse signals having a phase difference which varies according to a rotational direction of a rotary drive means provided in said horizontal scanning means;

causing said horizontal scanning direction to depend on the rotational direction of said rotary drive means;

detecting reversal of the rotational direction of said rotary drive means, based on said phase difference between said two rotational angle pulse signals;

detecting said rotational angle pulse signals from said reversal of the rotational direction; and detecting a reading start point which starts reading said sample, based on the detected rotational angle pulse signals.

4. The method as set forth in claim 3, wherein timing at which the rotational direction of said rotary drive means is switched is changed according to a length in said horizontal scanning direction of said medium.

5. A scanner for detecting a reading start point which starts reading information in a horizontal scanning direction or a recording start point which starts recording information in said horizontal scanning direction, by relatively moving a predetermined medium to be scanned and/or a scan head, which reads said information from said medium or records said information on said medium, by horizontal scanning means so that said scan head can reiteratively perform horizontal scanning in a fixed direction with respect to said medium, said scanner comprising:

rotary drive means having angle signal generation means for generating two rotational angle pulse signals having a phase difference which varies according to a rotational direction of said rotary drive means, said rotary drive means being provided in said horizontal scanning means and said horizontal scanning direction being dependent on the rotational direction of said rotary drive means;

rotational direction detection means for detecting the rotational direction of said rotary drive means and reversal of said rotational direction, based on said phase difference between said two rotational angle pulse signals; and scanning-start-point detection means for detecting said rotational angle pulse signals from said reversal detected by said rotational direction detection means, and detecting said scanning start point, based on the detected rotational angle pulse signals.

6. The scanner as set forth in claim 5, wherein said rotary drive means changes timing at which said rotational direction is switched in accordance with a length in said horizontal scanning direction of said medium.

7. An image information reader comprising:

an exciting light source for emitting exciting light;

an optical head for emitting said exciting light to a predetermined sample;

horizontal scanning means for relatively moving said optical head and/or said sample so that said exciting light can repeatedly perform horizontal scanning by a predetermined length in a fixed direction with respect to said sample;

vertical scanning means for relatively moving said optical head and/or said sample in a direction substantially perpendicular to a direction of said horizontal scanning so that said exciting light can perform vertical scanning with respect to said sample;

photoelectric read means for photoelectrically reading out luminescence emitted from said sample irradiated with said exciting light by said relative scanning;

rotary drive means having angle signal generation means for generating two rotational angle pulse signals having a phase difference which varies according to a rotational direction of said rotary drive means, said rotary drive means being provided in said horizontal scanning means and said horizontal scanning direction being dependent on the rotational direction of said rotary drive means;

rotational direction detection means for detecting the rotational direction of said rotary drive means and reversal of said rotational direction, based on said phase difference between said two rotational angle pulse signals; and reading-start-point detection means for detecting said rotational angle pulse signals from said reversal detected by said rotational direction detection means, and detecting a reading start point which starts reading said sample, based on the detected rotational angle pulse signals.

8. The image information reader as set forth in claim 7, wherein said rotary drive means changes timing at which said rotational direction is switched in accordance with a length in said horizontal scanning direction of said sample.

9. A method of detecting a reading start point which starts reading information in a horizontal scanning direction or a recording start point which starts recording information in said horizontal scanning direction, by relatively moving a predetermined medium to be scanned and/or a scan head, which reads said information from said medium or records said information on said medium, in the going and returning directions by horizontal scanning means so that said scan head can reiteratively perform horizontal scanning in a fixed direction with respect to said medium, said method comprising the steps of:

detecting a scanning start point which starts scanning said medium in said going direction of said horizontal scanning;

measuring a moved distance in said going direction of said medium and/or said scan head between a scanning end point, which ends said scanning, and reversal of a moving direction of said medium and/or said scan head from said going direction to said returning direction, said scanning end point previously being set according to a length in said horizontal scanning direction of said medium;

measuring a moved distance in said returning direction of said medium and/or said scan head from the reversal of the moving direction of said medium and/or said scan head; and detecting a position, where said moved distance in said returning direction coincides with said moved distance measured in said going direction, as a scanning start point in said returning direction.

10. The method as set forth in claim 9, wherein said scanning end point is set based on a distance moved from the detected scanning start point in said going direction.

11. The method as set forth in claim 9, wherein said moved distance in said returning direction of said medium and/or said scan head, measured from the reversal of the moving direction of said medium and/or said scan head, is corrected by a previously obtained free running distance at the time of said reversal, and a position, where the corrected moved distance in said returning direction coincides with said moved distance measured in said going direction, is detected as said scanning start point in said returning direction.

12. The method as set forth in claim 10, wherein said moved distance in said returning direction of said medium and/or said scan head, measured from the reversal of the moving direction of said medium and/or said scan head, is corrected by a previously obtained free running distance at the time of said reversal, and a position, where the corrected moved distance in said returning direction coincides with said moved distance measured in said going direction, is detected as said scanning start point in said returning direction.

13. A method of photoelectrically reading out luminescence emitted from a predetermined sample irradiated with exciting light, by relatively moving said exciting light and/or said sample within a fixed range in the going and returning directions so that said exciting light can reiteratively perform horizontal scanning relatively with respect to said sample and by relatively moving said exciting light and/or said sample in a direction substantially perpendicular to a direction of said horizontal scanning so that said exciting light can perform vertical scanning with respect to said sample, said method comprising the steps of:

detecting a reading start point which starts reading said luminescence in said going direction of said horizontal scanning;

reading out said luminescence photoelectrically, while said exciting light is scanning said sample from the detected reading start point to a reading end point which ends said reading, said reading end point previously being set according to a length in said horizontal scanning direction of said sample;

measuring a moved distance in said going direction of said exciting light and/or said sample between said reading end point and reversal of a moving direction of said exciting light and/or said sample from said going direction to said returning direction;

measuring a moved distance in said returning direction of said exciting light and/or said sample from said reversal of the moving direction of said exciting light and/or said sample; and starting reading said luminescence photoelectrically in said returning direction from a position where said moved distance in said returning direction coincides with said moved distance measured in said going direction.

14. The method as set forth in claim 13, wherein said reading end point is set based on a distance moved from the detected reading start point in said going direction.

15. The method as set forth in claim 13, wherein said moved distance in said returning direction of said exciting light and/or said sample, measured from the reversal of the moving direction of said exciting light and/or said sample, is corrected by a previously obtained free running distance at the time of said reversal, and reading said luminescence photoelectrically in said returning direction is started from a position where the corrected moved distance in said returning direction coincides with said moved distance measured in said going direction.

16. The method as set forth in claim 14, wherein said moved distance in said returning direction of said exciting light and/or said sample, measured from the reversal of the moving direction of said exciting light and/or said sample, is corrected by a previously obtained free running distance at the time of said reversal, and reading said luminescence photoelectrically in said returning direction is started from a position where the corrected moved distance in said returning direction coincides with said moved distance measured in said going direction.

17. A scanner for detecting a reading start point which starts reading information in a horizontal scanning direction or a recording start point which starts recording information in said horizontal scanning direction, by relatively moving a predetermined medium to be scanned and/or a scan head, which reads said information from said medium or records said information on said medium, in the going and returning directions by horizontal scanning means so that said scan head can reiteratively perform horizontal scanning in a fixed direction with respect to said medium, said scanner comprising:

reversal detection means for detecting that a moving direction of said medium and/or said scan head being moved by said horizontal scanning means has been reversed from said going direction to said returning direction;

first scanning-start-point detection means for detecting a scanning start point in said going direction of said horizontal scanning which is performed by said horizontal scanning means;

first offset measurement means for measuring a moved distance in said going direction of said medium and/or said scan head between a scanning end point which ends scanning, set according to a length in said horizontal scanning direction of said medium, and said reversal;

second offset measurement means for measuring a moved distance in said returning direction of said medium and/or said scan head from said reversal detected by said reversal detection means; and second scanning-start-point detection means for detecting a horizontal scanning position, where said moved distance in said returning direction detected by said second offset measurement means coincides with said moved distance in said going direction detected by said first offset measurement means, as a scanning start point in said returning direction.

18. The scanner as set forth in claim 17, wherein said scanning end point is set based on a distance moved from said scanning start point detected by said first scanning-start-point detection means.

19. The scanner as set forth in claim 17, wherein said second scanning-start-point detection means detects said scanning start point in said returning direction, by correcting said moved distance in said returning direction, detected by said second offset measurement means, by a previously obtained free running distance at the time of said reversal corresponding to backlash of said horizontal scanning means.

20. The scanner as set forth in claim 18, wherein said second scanning-start-point detection means detects said scanning start point in said returning direction, by correcting said moved distance in said returning direction, detected by said second offset measurement means, by a previously obtained free running distance at the time of said reversal corresponding to backlash of said horizontal scanning means.

21. The scanner as set forth in claim 17, wherein said horizontal scanning means is equipped with rotary drive means having rotational directions on which the moving directions of said medium and/or said scan head in said going and returning directions depend, and also having a rotational angle on which said moved distance depends; and said first and second offset measurement means measure said moved distance by detecting said rotational angle.

22. The scanner as set forth in claim 18, wherein said horizontal scanning means is equipped with rotary drive means having rotational directions on which the moving directions of said medium and/or said scan head in said going and returning directions depend, and also having a rotational angle on which said moved distance depends; and said first and second offset measurement means measure said moved distance by detecting said rotational angle.

23. The scanner as set forth in claim 19, wherein said horizontal scanning means is equipped with rotary drive means having rotational directions on which the moving directions of said medium and/or said scan head in said going and returning directions depend, and also having a rotational angle on which said moved distance depends; and said first and second offset measurement means measure said moved distance by detecting said rotational angle.

24. The scanner as set forth in claim 20, wherein said horizontal scanning means is equipped with rotary drive means having rotational directions on which the moving directions of said medium and/or said scan head in said going and returning directions depend, and also having a rotational angle on which said moved distance depends; and said first and second offset measurement means measure said moved distance by detecting said rotational angle.

25. An image information reader comprising:

an exciting light source for emitting exciting light;

an optical head for emitting said exciting light to a predetermined sample;

horizontal scanning means for relatively moving said exciting light and/or said sample within a fixed range in the going and returning directions so that said exciting light can reiteratively perform horizontal scanning with respect to said sample;

vertical scanning means for relatively moving said exciting light and/or said sample in a direction substantially perpendicular to a direction of said horizontal scanning so that said exciting light can perform vertical scanning with respect to said sample;

photoelectric read means for photoelectrically reading out luminescence emitted from said sample irradiated with said exciting light by said relative scanning;

reversal detection means for detecting that a moving direction of said exciting light and/or said sample being moved by said horizontal scanning means has been reversed from said going direction to said returning direction;

first reading-start-point detection means for detecting a reading start point which starts reading said luminescence in said going direction of said horizontal scanning which is performed by said horizontal scanning means;

first offset measurement means for measuring a moved distance in said going direction of said exciting light and/or said sample between a reading end point which ends reading, set according to a length in said horizontal scanning direction of said sample, and said reversal;

second offset measurement means for measuring a moved distance in said returning direction of said exciting light and/or said sample from said reversal detected by said reversal detection means; and second reading-start-point detection means for detecting a horizontal scanning position, where said moved distance in said returning direction detected by said second offset measurement means coincides with said moved distance in said going direction detected by said first offset measurement means, as a reading start point which starts said reading in said returning direction;

wherein said photoelectric read means starts said reading from said reading start points in said going and returning directions.

26. The image information reader as set forth in claim 25, wherein said reading end point is set based on a distance moved from said reading start point detected by said first reading-start-point detection means.

27. The image information reader as set forth in claim 25, wherein said second reading-start-point detection means detects said reading start point in said returning direction, by correcting said moved distance in said returning direction, detected by said second offset measurement means, by a previously obtained free running distance at the time of said reversal corresponding to backlash of said horizontal scanning means.

28. The image information reader as set forth in claim 26, wherein said second reading-start-point detection means detects said reading start point in said returning direction, by correcting said moved distance in said returning direction, detected by said second offset measurement means, by a previously obtained free running distance at the time of said reversal corresponding to backlash of said horizontal scanning means.

29. The image information reader as set forth in claim 25, wherein said horizontal scanning means is equipped with rotary drive means having rotational directions on which the moving directions of said exciting light and/or said sample in said going and returning directions depend, and also having a rotational angle on which said moved distance depends; and said first and second offset measurement means measure said moved distance by detecting said rotational angle.

30. The image information reader as set forth in claim 26, wherein said horizontal scanning means is equipped with rotary drive means having rotational directions on which the moving directions of said exciting light and/or said sample in said going and returning directions depend, and also having a rotational angle on which said moved distance depends; and said first and second offset measurement means measure said moved distance by detecting said rotational angle.

31. The image information reader as set forth in claim 27, wherein said horizontal scanning means is equipped with rotary drive means having rotational directions on which the moving directions of said exciting light and/or said sample in said going and returning directions depend, and also having a rotational angle on which said moved distance depends; and said first and second offset measurement means measure said moved distance by detecting said rotational angle.

32. The image information reader as set forth in claim 28, wherein said horizontal scanning means is equipped with rotary drive means having rotational directions on which the moving directions of said exciting light and/or said sample in said going and returning directions depend, and also having a rotational angle on which said moved distance depends; and said first and second offset measurement means measure said moved distance by detecting said rotational angle.

* * * * *